US009817001B2

(12) United States Patent
Asztalos et al.

(10) Patent No.: US 9,817,001 B2
(45) Date of Patent: Nov. 14, 2017

(54) METHODS FOR DETERMINING LDL CHOLESTEROL TREATMENT

(71) Applicant: Boston Heart Diagnostics Corporation, Framingham, MA (US)

(72) Inventors: Bela F. Asztalos, Framingham, MA (US); Ernst J. Schaefer, Natick, MA (US)

(73) Assignee: BOSTON HEART DIAGNOSTICS CORPORATION, Framingham, MA (US)

( * ) Notice: Subject to any disclaimer, the term of this patent is extended or adjusted under 35 U.S.C. 154(b) by 0 days.

(21) Appl. No.: 13/945,436

(22) Filed: Jul. 18, 2013

(65) Prior Publication Data
US 2014/0088072 A1  Mar. 27, 2014

Related U.S. Application Data

(63) Continuation of application No. 13/658,387, filed on Oct. 23, 2012, now abandoned, which is a continuation of application No. 12/472,351, filed on May 26, 2009, now abandoned.

(60) Provisional application No. 61/056,163, filed on May 27, 2008, provisional application No. 61/084,909, filed on Jul. 30, 2008.

(51) Int. Cl.
G01N 33/92 (2006.01)
(52) U.S. Cl.
CPC ......... *G01N 33/92* (2013.01); *G01N 2800/52* (2013.01)
(58) Field of Classification Search
CPC ..... C12Q 1/60; G01N 33/92; G01N 2800/044
USPC ........................................... 435/11
See application file for complete search history.

(56) References Cited

U.S. PATENT DOCUMENTS

| 3,703,591 | A | 11/1972 | Bucolo |
| 4,245,041 | A | 1/1981 | Denney |
| 4,330,299 | A | 5/1982 | Cerami |
| 4,495,279 | A | 1/1985 | Karpetsky et al. |
| 4,683,195 | A | 7/1987 | Mullis et al. |
| 4,683,202 | A | 7/1987 | Mullis |
| 4,800,159 | A | 1/1989 | Mullis et al. |
| 4,999,289 | A | 3/1991 | Akiba et al. |
| 5,223,392 | A | 6/1993 | Cohen |
| 5,436,149 | A | 7/1995 | Barnes |
| 5,843,663 | A | 12/1998 | Stanley et al. |
| 5,849,481 | A | 12/1998 | Urdea et al. |
| 5,849,486 | A | 12/1998 | Heller et al. |
| 5,851,772 | A | 12/1998 | Mirzabekov et al. |
| 5,888,827 | A | 3/1999 | Kayahara et al. |
| 5,900,481 | A | 5/1999 | Lough et al. |
| 5,919,626 | A | 7/1999 | Shi et al. |
| 5,955,351 | A | 9/1999 | Gerdes et al. |
| 6,194,164 | B1 | 2/2001 | Matsui et al. |
| 6,316,196 | B1 | 11/2001 | Morten |
| 6,410,309 | B1 | 6/2002 | Barbera-Guillem et al. |
| 6,582,908 | B2 | 6/2003 | Fodor et al. |
| 7,417,039 | B2 * | 8/2008 | Davis .............................. 514/183 |
| 7,435,541 | B2 | 10/2008 | Olson et al. |
| 7,608,405 | B2 | 10/2009 | Ebinuma et al. |
| 7,659,107 | B2 | 2/2010 | Smith et al. |
| 7,700,277 | B2 | 4/2010 | Ambrose et al. |
| 7,871,789 | B2 | 1/2011 | Yonehara et al. |
| 8,003,795 | B2 | 8/2011 | Liu et al. |
| 8,026,345 | B2 | 9/2011 | Burghardt et al. |
| 8,093,222 | B2 * | 1/2012 | Freier et al. ................. 514/44 A |
| 8,470,541 | B1 | 6/2013 | Asztalos et al. |
| 2003/0143223 | A1 | 7/2003 | Cabezas et al. |
| 2004/0131658 | A1 | 7/2004 | Kaput |
| 2004/0259179 | A1 * | 12/2004 | Assmann et al. ............... 435/11 |
| 2005/0054005 | A1 | 3/2005 | Ellis et al. |
| 2005/0059581 | A1 | 3/2005 | Mantzoros |
| 2005/0281868 | A1 | 12/2005 | Lane |
| 2006/0293225 | A1 | 12/2006 | Dialynas et al. |
| 2007/0003600 | A1 * | 1/2007 | Moore et al. ................. 424/439 |
| 2007/0015291 | A1 | 1/2007 | Smith |
| 2007/0031838 | A1 | 2/2007 | Ambrose et al. |

(Continued)

FOREIGN PATENT DOCUMENTS

| EP | 1186672 A2 | 3/2002 |
| EP | 1651774 B1 | 9/2007 |

(Continued)

OTHER PUBLICATIONS

Schaefer E. et al. Association of Statin Potency with Markers of Cholesterol Absorption/Synthesis and LDL-C Lowering Efficacy of Ezetimibe Add on Therapy. J of Clinical Lipidology 6(3)286 abstract 160, Jun. 2012.*
Sasahara T. et al. Altered Properties of HDL Subfractions in Obese Subjects. J of Lipid Research 38:600-611, 1997.*
Dayspring T. HDL Classification. www.lipidcenter.com No date given.*

(Continued)

*Primary Examiner* — Ralph Gitomer
(74) *Attorney, Agent, or Firm* — Brown Rudnick LLP; Thomas C. Meyers

(57) ABSTRACT

Disclosed is a personalized diagnostic and treatment solution for cardiovascular disease. The invention comprises methods for devising a personalized treatment plan for a patient via the use of an extended CVD risk assessment panel measuring markers of cholesterol absorption and production and HDL subfractions. This solution provides a more complete risk assessment of an individual than merely measuring traditional CVD risk markers alone, and enables the healthcare practitioner to optimize therapy for patients with or without established CVD. This solution presents the advantages of greater accuracy, savings in time and cost over existing testing and treatment methods.

6 Claims, 21 Drawing Sheets

(56) References Cited

U.S. PATENT DOCUMENTS

| | | |
|---|---|---|
| 2007/0059722 A1 | 3/2007 | Salonen et al. |
| 2007/0196841 A1 | 8/2007 | Ruano et al. |
| 2007/0218519 A1 | 9/2007 | Urdea et al. |
| 2008/0227210 A1 | 9/2008 | Smith |
| 2008/0293054 A1 | 11/2008 | Medina et al. |
| 2008/0300170 A1 | 12/2008 | Gelber et al. |
| 2009/0197242 A1 | 8/2009 | Kaddurah-Daouk et al. |
| 2009/0246801 A1 | 10/2009 | Smith |
| 2010/0063153 A1 | 3/2010 | Chatterjee et al. |
| 2010/0076787 A1 | 3/2010 | Naylor et al. |
| 2010/0120136 A1 | 5/2010 | Larsen et al. |
| 2010/0167306 A1 | 7/2010 | Smith |
| 2010/0190172 A1 | 7/2010 | Cargill et al. |
| 2010/0204557 A1 | 8/2010 | Kiaie et al. |
| 2011/0112186 A1 | 5/2011 | Link et al. |
| 2011/0250618 A1 | 10/2011 | Nelson et al. |
| 2011/0269735 A1 | 11/2011 | Shiffman et al. |
| 2012/0065514 A1* | 3/2012 | Naghavi et al. ............... 600/454 |
| 2014/0308683 A1* | 10/2014 | Kane .................. G01N 33/6893 435/7.92 |

FOREIGN PATENT DOCUMENTS

| | | |
|---|---|---|
| WO | 02/48715 | 6/2002 |
| WO | 2004/050898 A2 | 6/2004 |
| WO | WO-2005/012566 A2 | 2/2005 |
| WO | WO-2006/008656 A2 | 1/2006 |
| WO | WO-2006/072654 A1 | 7/2006 |
| WO | WO-2007/012884 A1 | 2/2007 |
| WO | WO-2007/061995 A2 | 5/2007 |
| WO | 2007/128884 A1 | 11/2007 |
| WO | 2008/131224 A2 | 10/2008 |
| WO | WO-2009/106838 A1 | 9/2009 |
| WO | WO-2011/058232 A1 | 5/2011 |
| WO | 2013/056087 A2 | 4/2013 |
| WO | WO-2013/078122 A1 | 5/2013 |

OTHER PUBLICATIONS

Rye K. et al. Formation and Metabolism of Prebeta Migrating Lipid Poor Apo A1. Arteriosclerosis, Thrombosis, and Vascular Biology 24:421-428, Mar. 2004.*

Sharrett A. et al. Coronary Heart Disease Prediction from Lipoprotein Cholesterol Levels . . . Circulation 104:1108-1113, 2001.*

Ahern et al., Biochemical, Reagent Kits Offer Scientists Good Return on Investment, The Science, vol. 9, pp. 1-5, 1995.

Armitage, J., "The safety of statins in clinical practice," Lancet, 2007, pp. 1781-1790, vol. 370.

Assmann G, Kannenberg F, Ramey DR, Musliner TA, Gutkin SW, Veltri EP. Effects of ezetimibe, simvastatin, atorvastatin, and ezetimibe-statin therapies on non-cholesterol sterols in patients with primary hypercholesterolemia. Curr Med Res Opin 2008;24:249-59.

Asztalos B F et al: "LpA-I, LpA-I:A-II HDL and CHD-risk: The Framingham Offspring Study and the Veterans Affairs HDL Intervention Trial", Atherosclerosis, vol. 188, No. 1, Sep. 1, 2006 (Sep. 1, 2006), pp. 59-67, XP028071474, Elsevier Ireland LTD, Dublin ISSN: 0021-9150, DOI: 10.1016/J.Atherosclerosis.Oct. 18, 2005.

Asztalos, B.F., et al., "Distribution of ApoA-I-containing HDL Subpopulations in Patients with Coronary Heart Disease," Arterioscler Thromb Vasc Biol., Dec. 2000; 20(12)2670-6.

Asztalos, B.F., et al., "High-density Lipoprotein Subpopulation Profile and Coronary Heart Disease Prevalence in Male Participants of the Framingham Offspring Study," Arterioscler Thromb Vasc Biol., Nov. 2004; 24(11):2181-7.

Asztalos, B.F., et al., "Two-dimensional electrophoresis of plasma lipoproteins: recognition of new apo A-I-containing subpopulations," Biochim Biophys Acta., Sep. 8, 1993; 1169(3):291-300.

Asztalos, B.F., et al., "Value of High-Density Lipoprotein (HDL) Subpopulations in Predicting Recurrent Cardiovascular Events in the Veterans Affairs HDL Intervention Trial," Arterioscler Thromb Vasc Biol., Oct. 2005; 25(10):2185-2191.

Ballantyne et al. Effect of ezetimibe coadministered with atorvastatin in 628 patients with primary hypercholesterolemia: a prospective, randomized, double-blind trial. Circulation 2003;107:2409-15.

Ballantyne, C.M., et al., "Risk for myopathy with statin therapy in high-risk patients," Arch Intern Med, 2003, pp. 553-564, vol. 163.

Barrett, J.C., et al., Haploview: analysis and visualization of LD and haplotype maps, Bioinformatics, 2005, pp. 263-265, vol. 21.

Bland et al., "Multiple significance tests: the Bonferroni method," BMJ, vol. 310, p. 170, Jan. 21, 1995.

Burke et al.,Mechanisms of the Liebermann-Burchard and Zak Color Reactions for Cholesterol, Clin. Chem .20(7), 794-801, 1974.

Burke, J. P., et al., "Rapid Rise in the Incidence of Type 2 Diabetes From 1987 to 1996," (1999) Arch Intern Med. 159:1450-1456.

Camont et al: "Biological activities of HDL subpopulations and their relevance to cardiovascular disease", Trends in Molecular Medicine, vol. 17, No. 10, Oct. 1, 2011.

Carlton et al., "Functional single nucleotide polymorphism-based association studies," Human Genomics, 2(6): 391-402 (2006).

Catapano AL, Reiner Z, De Backer G, et al. ESC/EAS Guidelines for the management of dyslipidaemias The Task Force for the management of dyslipidaemias of the European Society of Cardiology (ESC) and the European Atherosclerosis Society (EAS). Atherosclerosis 2011;217:3-46.

Cholesterol Treatment Trialists' (CTT) Collaborators, Efficacy and safety of cholesterol-lowering treatment: prospective meta-analysis of data from 90,056 participants in 14randomised trials of statins, Lancet, 2005, pp. 1267-1278, vol. 366.

Corsini, A., et al., "Pharmacokinetic interactions between statins and fibrates," Am J. Cardiol, 2005,pp. 44K-49K, vol. 96.

Couvert P et al, Association between a Frequent Allele of the Gene Encoding OATP1B1 and the Enhanced LDL-Lowering Response to Fluvastatin Therapy, Pharmacogenomics 9: 1217-1227, 2008.

Cuyper et al., Determination of changes in serum lathosterol during treatment with simvastatin to evaluate the role of lathosterol as a parameter for whole body cholesterol synthesis. Clin Chim Acta 1993;219:123-30.

Davidson MH, Ballantyne CM, Kerzner B, et al. Efficacy and safety of ezetimibe coadministered with statins: randomised, placebo-controlled, blinded experience in 2382 patients with primary hypercholesterolemia. Int J Clin Pract 2004;58:746-55.

Davidson MH, McGarry T, Bettis R, et al. Ezetimibe coadministered with simvastatin in patients with primary hypercholesterolemia. J Am Coll Cardiol 2002;40:2125-34.

Davis, H et al. Zetia: Inhibition of Niemann-Pick C1 Like 1 (NPC1L1) To Reduce Intestinal Cholesterol Absorption and Treat Hyperlipidemia. Journal of Atherosclerosis and Thrombosis. May 2007, vol. 14; pp. 99-108.

De Cuyper I, Wolthers BG, van Doormaal JJ, Wijnandts PN. Determination of changes in serum lathosterol during treatment with simvastatin to evaluate the role of lathosterol as a parameter for whole body cholesterol synthesis. Clin Chim Acta 1993;219:123-30.

Deepak Voora et al., The SLCO1B18*5 Genetic Variant is Associated with Statin-Induced Side Effects, Journal of the American College of Cardiology, vol. 54, No. 17, 2009, pp. 1609-1616.

Devlin, B., et al., "Genomic control for association studies," Biometrics, 1999, pp. 997-1004, vol. 55.

Dullaart RPF et al, The Serum Lathosterol to Cholesterol Ratio, an Index of Cholesterol Synthesis,is Not Elevated in Patients With Glomerular Proteinuria and Is Not Associated With Improvement of Hyperlipidemia in Response to Antiproteinuric Treatment, Metabolism 45: 723-730, 1996.

Espy et al (2006) Clin Microbiol Rev. Jan. 2006; 19(1): 165-256.

Farnier, M et al. Lipid-Altering Eficacy of Ezetimibe/Simvastatin 10/20 mg Compared With Rosuvastatin 10 mg in High-Risk Hypercholesterolaemic Patients Inadequately Controlled With Prior Statin Monotherapy—The IN-CROSS Study. The International Journal of Clinical Practice. Apr. 2009, vol. 63; pp. 547-559.

(56) References Cited

OTHER PUBLICATIONS

Fiegenbaum et al., "The role of common variants of ABCB1, CYP3A4, and CYP3A5 genes in lipidlowering efficacy and safety of simvastatin treatment," Clin. Pharmocol. Ther., vol. 78, pp. 551-558, 2005.
Friedewald WT, Levy RI, Fredrickson DS. Estimation of the concentration of low-density lipoprotein cholesterol in plasma, without use of the preparative ultracentrifuge. Clin Chem 1972;18:499-502.
Frudakis et al., "CYP2D6*4 polymorphism is associated with statin-induced muscle effects," Pharmacogenetics and Genomics, vol. 17, pp. 695-707, 2007.
Gagne et al., Efficacy and safety of ezetimibe coadministered with atorvastatin or simvastatin in patients with homozygous familial hypercholesterolemia. Circulation 2002;105:2469-75.
Gazi IF et al, Effect of Ezetimibe in Patients Who cannot Tolerate Statins or cannot Get to the Low Density Lipoprotein Cholesterol Target Despite Taking a Statin, Crur Med Res Opin 23: 2183-2192, 2007.
Generaux GT et al, Impact of SLCOIB1 (OATP1B1) and ABCG2 (BCRP) Genetic Polymorphisms and Inhibition on LDL-C Lowering and Myopathy of Statins, Xenobiot 41: 639-651, 2011.
Goh et al., HPLC analysis of desmosterol, 7-dehydrocholesterol, and cholesterol. Lipids 24.7 (1989): 652-655.
Gordon, D.J. et al., "High-density Lipoprotein Cholesterol and Cardiovascular Disease. Four Prospective American Studies," Circulation, Jan. 1989; 79(1):8-15.
Gouni et al. Effects of ezetimibe and/or simvastatin on LDL receptor protein expression and on LDL receptor and HMG-CoA reductase gene expression: a randomized trial in healthy men. Atherosclerosis 2008;198:198-207.
Grundy et al. Implications of recent clinical trials for the National Cholesterol Education Program Adult Treatment Panel III guidelines. Circulation 2004;110:227-39.
Grundy et al., "Plasma Non-Cholesterol Sterols as Indicators of Cholesterol Absorption." Journal of lipid research (2013) V54 873-875.
Gunderson, K.L., et al., "Whole-genome genotyping of haplotype tag single nucleotide polymorphisms," Pharmacogenomics, 2006, pp. 641-648, vol. 7.
Havekes LM et al. A rapid micro method for apolipoprotein E phenotyping directly in serum. J Lipid Res (1987) 28:455-63.
Heart Protection Study Collaborative Group, "MRC/BHF Heart Protection Study of cholesterol lowering with simvastatin in 20,536 high-risk individuals: a randomised placebo-controlled trial," Lancet, 2002, pp. 7-22, vol. 360.
Hermann et al., "Pharmacokinetics and Drug Disposition: Exposure of atorvastatin is unchangedbut lactone and acid metabolites are increased several-fold in patients with atorvastatin-induced myopathy," Clinical Pharmacology & Therapeutics, vol. 79, No. 6, pp. 532-539, 2006.
Himbergen et al., Comparison of the effects of maximal dose atorvastatin and rosuvastatin therapy on cholesterol synthesis and absorption markers. J Lipid Res 2009;50:730-9.
Hironobu Akao et al., Genetic Variation at the SLC01B1 Gene Locus and Low Density Lipoprotein Cholesterol Lowering Response to Pravastatin in the Elderly, Atherosclerosis, 220, 2012, pp. 413-417.
Ho et al., "Drug and Bile Acid Transporters in Rosuvastatin Hepatic Uptake: Function, Expression, and Pharmacogenetics," Gastroenterology, 130(6): 1793-1806 (2006).
Hsiang et al., "A Novel Human Hepatic Organic Anion Transporting Polypeptide (OATP2): Identification of a liver-specific human organic anion transporting polypeptide and identification of rat and human hydroxymethylglutaryl-CoA reductase inhibitor transporters," J. Biol. Chem., 274(52): 37161-37168 (1999).
International Hapmap Consortium, "A haplotype map of the human genome," Nature, 2005,pp. 1299-1320, vol. 437.
International Search Report for PCT/GB2009/000547, dated May 11, 2009, 4 pages.
International Search Report and Written Opinion for PCT/US12/60014, dated Apr. 5, 2013, 9 pages.
International Search Report and Written Opinion for PCT/US2013/066860 dated Jan. 20, 2014, 14 pages.
International Search Report and Written Opinion for PCT/US2013/62241 dated Jan. 17, 2014, 16 pages.
Isbell et al: "Reproducibility and Reliability of Atherosclerotic Plaque Volume Measurements in Peripheral Arterial Disease with Cardiovascular Magnetic Resonance", Journal of Cardiovascular Magnetic Resonance, vol. 9, No. 1, Jan. 1, 2007, p. 1-15.
Jakulj et al. Baseline cholesterol absorption and the response to ezetimibe/simvastatin therapy: a post-hoc analysis of the ENHANCE trial. J Lipid Res 2010;51:755-62.
Jones et al. Comparison of the efficacy and safety of rosuvastatin versus atorvastatin, simvastatin, and pravastatin across doses (STELLAR* Trial). Am J Cardiol 2003;92:152-60.
Juraschek et al., Alternative Markers of Hyperglycemia and Risk of Diabetes, vol. 35 No. 11, Aug. 8, 2012, p. 1-6.
Kajinami, K., et al., "CYP3A4 genotypes and plasma lipoprotein levels before and after treatment with atorvastatin in primary hypercholesterolemia," Am J Cardiol, 2004, pp. 104-107, vol. 93.
Kameyama et al., "Functional characterization of SLC01B1 (OATP-C) variants, SLC01B1*5,SLC01B1*15 and SCL01B1*15+C1007G, by using transient expression systems of HeLa and HEK293 cells," Pharmacogenetics and Genomics, vol. 15, No. 7, pp. 513-522. Jul. 2005.
Kim et. al., "3-Hydroxy-3-methylglutaryl-coenzyme A reductase inhibitors (statins) and genetic variability(single nucleotide polymorphisms) in a hepatic drug uptake transporter: What's it all about?," Clinical Pharmacology & Therapeutics, vol. 75, No. 5, pp. 381-385, 2004.
Kim, K.T., et al., "Increased systemic exposure to rosuvastatin in Asian subjects residing in the United States compared to Caucasian subjects," Clinical Pharmacology and Therapeutics, 2008, p. S 14,vol. 83.
Kivistö et al: "Influence of Drug Transporter Polymorphisms on Pravastatin Pharmacokinetics in Humans" Pharmaceutical Research, Kluwer Academic Publishers-Plenum Publishers, NE, vol. 24, No. 2, Dec. 20, 2006, pp. 239-247.
Kolberg, J. A., et al., "Development of a Type 2 Diabetes Risk Model From a Panel of Serum Biomarkers From the Inter99 Cohort," (2009) Diabetes Care 32(7):1207-12.
Konig, J., et al., Pharmacogenomics of human OATP transporters, Naunyn Schmiedebergs Arch Pharmacol2006, pp. 432-443, vol. 372.
Lakoski SG, Xu F, Vega GL, et al. Indices of Cholesterol Metabolism and Relative Responsiveness to Ezetimibe and Simvastatin. J Clin Endocrinol Metab 2010;95:800-9.
Lamon-Fava S, Diffenderfer MR, Barrett PH, et al. Effects of different doses of atorvastatin on human apolipoprotein B-100, B-48, and A-I metabolism. J Lipid Res 2007;48:1746-53.
Law, M., et al., "Statin safety: a systematic review," Am J. Cardiol, 2006, pp. S52-S60, vol. 97.
Link et al., "SLC01B1 Variants and Statin-Induced Myopathy—A Genomewide Study," N. Engl. J. Med., 359: 789-799 (2008).
Lund, E., et al. "Determination of serum levels of unesterified lathosterol by isotope dilution-mass spectrometry." Scandinavian journal of clinical & laboratory investigation 49.2 (1989): 165-171.
Luzón-Toro et al., "Gas chromatographic-mass spectrometric determination of brain levels of α-cholest-8-en-3β-ol (lathosterol)." Journal of Chromatography B 850.1 (2007): 177-182.
Mangravite, L.M., et al., "Clinical implications of pharmacogenomics of statin treatment," Pharmacogenomics J, 2006, pp. 360-374, vol. 6.
Mann, D. M., et al., "The Multi-Ethnic Study of Atherosclerosis," (MESA) (2010) Am J Epidemiol 171(9):980-988. Jan. 2010.
Matthan NR et al., Impact of simvastatin, niacin, and/or antioxidants on cholesterol metabolism in CAD patients with low HDL. J Lipid Res. 2003;44:800-806.
Matthan NR et al., "Deuterium uptake and plasma cholesterol precursor levels correspond as methods for measurement of endogenous cholesterol synthesis in hypercholesterolemic women.", Lipids. 2000;35:1037-1044.

(56) References Cited

OTHER PUBLICATIONS

Matthan, N et al. Cholesterol Absorption and Synthesis Markers in Individuals With and Without a CHD Event During Pravastatin Therapy: Insights From The PROSPER Trial. Journal of Lipid Research. Jul. 3, 2009, vol. 51; pp. 202-209.
Miettinen et al., Noncholesterol sterols and cholesterol lowering by long-term simvastatin treatment in coronary patients: relation to basal serum cholestanol. Arterioscler Thromb Vasc Biol 2000;20:1340-6.
Miettinen et al., Serum plant sterols and cholesterol precursors reflect cholesterol absorption and synthesis in volunteers of a randomly selected male population. Am J Epidemiol 1990;131:20-31.
Miettinen TA, Gylling H, Lindbohm N, Miettinen TE, Rajaratnam RA, Relas H. Serum noncholesterol sterols during inhibition of cholesterol synthesis by statins. J Lab Clin Med 2003;141:131-7.
Mikko Niemi et al., Organic Anion Transporting Polypeptide 1B1: a Genetically PolymorphicTransporter of Major Impotence for Hepatic Drug Uptake, Pharmacological Reviews, vol. 63, No. 1, 2011, pp. 157-181.
Molden, E., "Variability in Cytochrome P450-Mediated Metabolism of Cardiovascular Drugs: Clinical Implications and Practical Attempts to Avoid Potential Problems," Heart Drug, 2004, pp. 55-79, vol. 4.
Morimoto et al., "Candidate gene approach for the study of genetic factors involved in HMG-CoA reductase inhibitor-induced rhabdomyolysis," Eighteenth JSSX Annual Meeting, 8PE-32 (2003).
Morimoto et al; A Novel Variant Allele of OATP-C (SLCO1B1) Found in a Japan Patient with Pravastatin-induced Myopathy, Drug Metab. Pharmocokinet. vol. 19, pp. 453-455; 2004.
Morimoto, K, et al., "OATP-C(OATP01B1)*15 is associated with statin-induced myopathy in hypercholesterolemia patients," Clinical Pharmacology & Therapeutics, 2005, pp. P21-P21 vol. 77.
Morrone D, Weintraub WS, Toth PP, Hanson ME, Lowe RS, Lin J, Shah AK, and Tershakovec AM. Lipid-altering efficacy of ezetimibe plus statin and statin monotherapy and identification of factors associated with treatment response: A pooled analysis of over 21,000 subjects from 27 clinical trials. Atherosclerosis , in press. 2012.223, 251-261.
Mulder et al., "Association of polymorphism in the cytochrome CYP2D6 and the efficacy and tolerability of simvastatin," Clin. Pharmacol. Ther., vol. 70, pp. 546-551, 2001.
Márk, L et al., Change in the cholesterol metabolism associated with the combined inhibition of synthesis and absorption. Orvosi hetilap 148.14 (2007): 627.
Nauck et al., Clinical Chemistry Feb. 2002 vol. 48 No. 2 236-254.
Niemi et al., "Acute effects of pravastatin on cholesterol synthesis are associated with SLC01B1(encoding OATP1B1) haplotype *17," Pharmacogenet. Genomics, vol. 15, No. 5, pp. 303-309, May 15, 2005.
Niemi et al., "High plasma pravastatin concentrations are associated with single nucleotide polymorphisms and haplotypes of organic anion transporting polypeptide-C (OATP-C, SCL01B1)," Pharmacogenetics, 14: 429-440 (2004).
Nishizato et al., "Polymorphisms of OATP-C (SLC21A6) and OAT3 (SLC22A8) genes: Consequences for pravastatin pharmacokinetics," Clin. Pharmacol. Ther., 73(6): 554-565 (2003).
Nissinen et. al., Applicability of non-cholesterol sterols in predicting response in cholesterol metabolism to simvastatin and fluvastatin treatment among hypercholesterolemic men. Nutr Metab Cardiovasc Dis 2010;20:308-16.
Nozawa et al.,"Genetic Polymorphisms of Human Organic Anion Transporters OATP-C(SLC21A6) and OATP-B (SLC21A9): Allele Frequiences in the Japanese Population and Functional Analysis," The Journal of Pharmacology and Experimental Therapeutics, vol. 302, No. 2, pp. 2002.
Oh, J., et al., "Genetic determinants of statin intolerance," Lipids Health Dis, 2007, pp. 6:7.
Ooi et. al., Dose-dependent effect of rosuvastatin on apolipoprotein B-100 kinetics in the metabolic syndrome. Atherosclerosis 2008;197:139-46.
Ordovas JM et al, The APOE Locus and the Pharmacogenetics of Lipid Response, Cur Opin Lipidol 13: 113-117, 2002.
Pasanen et al., "Different Effects of SLC01B1 Polymorphism on the Pharmacokinetics of Atorvastatin and Rosuvastatin," Clin. Pharmacol. Ther., 82(6): 726-733 (2007).
Pasanen et al., "Global analysis of genetic variation in SLC01B1," Pharmacogenomics, vol. 9, No. 1, pp. 19-33, Jan. 2008.
Pasanen et al.,"SLC01B1 polymorphism markedly affects the pharmacokinetics of simvastatinacid," Pharmacogenet. Genomics, vol. 16, No. 12, pp. 873-879, Dec. 2006.
Pasanen et al.; Frequencies of single nucleotide polymorphisms and haplotypes of organic anion transporting polypeptide 1B1 SLCO1B1 gene in a Finnish population, Eur. J, Clin. pharmacol. vol. 62, pp. 409-415; 2006.
Pearson et al., Effectiveness of ezetimibe added to ongoing statin therapy in modifying lipid profiles and low-density lipoprotein cholesterol goal attainment in patients of different races and ethnicities: a substudy of the Ezetimibe add-on to statin for effectiveness trial. Mayo Clin Proc 2006;81:1177-85.
Pearson et. al., A community-based, randomized trial of ezetimibe added to statin therapy to attain NCEP ATP III goals for LDL cholesterol in hypercholesterolemic patients: the ezetimibe add-on to statin for effectiveness (EASE) trial. Mayo Clin Proc 2005;80:587-95.
Perk et al. European Guidelines on cardiovascular disease prevention in clinical practice (version 2012): The Fifth Joint Task Force of the European Society of Cardiology and Other Societies on Cardiovascular Disease Prevention in Clinical Practice Cardiovascular Prevention & Rehabilitation, Eur Heart J 2012;33:1635-701.
Price, A.L., et al., "Principal components analysis corrects for stratification in genome-wide association studies," Nat Genet, 2006, pp. 904-909, vol. 38.
Purcell, S., et al., "PLINK: a tool set for whole-genome association and population-based linkage analyses," Am J Hum Genet, 2007, pp. 559-575, vol. 81.
R Development Core Team, "R: A Language and Environment for Statistical Computing," Vienna, Austria: R Foundation for Statistical Computing, 2007.
Reihnér E, Rudling M, Ståhlberg D, et al. Influence of pravastatin, a specific inhibitor of HMG-CoA reductase, on hepatic metabolism of cholesterol. N Engl J Med 1990;323:224-8.
Robinson, "Simvastatin: present and future perspectives," Expert Opin. Pharmacother., 8(13): 2159-2172 (2007).
Romaine SPR et al, The Influence of SLC01B1 (OATP1B1) Gene Polymorphisms on Response to Statin Therapy,Pharmacogenom J 10: 1-11, 2010.
Ruano et al., Physiogenomic Association of Statin-Related Myalgia to Serotonin Receptors, Muscle Nerve, vol. 36, pp. 329-335, 2007.
Schaffer, R., et al. "Comparison of two isotope dilution/mass spectrometric methods for determination of total serum cholesterol." Clinical chemistry 28.1 (1982): 5-8.
Schmidt, M. I., et al., "The Atherosclerosis Risk in Communities study," (2005) Diabetes Care 28(8):2013-2018.
Search Study Collaborative Group, "Study of the effectiveness of additional reductions in cholesterol and homocysteine (SEARCH): characteristics of a randomized trial among 12064 myocardial infarction survivors," Am Heart J, 2007, pp. 815-823, vol. 154, No. e6.
Shitara et al., "Pharmacokinetic and pharmacodynamic alterations of 3-hydroxy-3-methylglutaryl coenzyme A (HMG-CoA) reductase inhibitors: drug-drug interactions and interindividual differences in transporter and metabolic enzyme functions," Pharmacol Ther, 2006, pp. 71-105, vol. 112.
Simonson, S.G., et al., "Rosuvastatin pharmacokinetics in heart transplant recipients administered an antirejection regimen including cyclosporine," Clin Pharmacol Ther, 2004, pp. 167-177, vol. 76.
Stern, M. P., et al., Predicting Diabetes, "Moving Beyond Impaired Glucose Tolerance," (1993) Diabetes 42:706-714.

(56) References Cited

OTHER PUBLICATIONS

Stern, M. P., et al., The San Antonio Heart Study, "Sex Difference in the Effects of Sociocultural Status on Diabetes and Cardiovascular Risk Factors in Mexican Americans," (1984) Am. J. Epidemiol. 120(6):834-851.
Streiner et al., "Correction for Multiple Testing, Is there a resolution?," Chest, vol. 140, No. 1, pp. 16-18, Jul. 2011.
Sudhop T, Lutjohann D, Kodal A, et al. Inhibition of intestinal cholesterol absorption by ezetimibe in humans. Circulation 2002;106:1943-8.
Sugiuchi et al., Clinical Chemistry 44:3 522-531 (1998).
The SEARCH Collaborative Group, The New England Journal of Medicine, SLC01B1 Variants and Statin-Induced Myopathy—A Genomewide Study, vol. 359, No. 8, Aug. 21, 2008, pp. 789-799.
Third Report of the National Cholesterol Education Program (NCEP) Expert Panel on Detection, Evaluation, and Treatment of High Blood Cholesterol in Adults (Adult Treatment Panel III) final report. Circulation 2002;106:3143-421.
Thompson, P.D., et al., "Statin-associated myopathy," JAMA, 2003, pp. 1681-1690, vol. 289.
Thongtang et al., "Effects of ezetimibe added to statin therapy on markers of cholesterol absorption and synthesis and LDL-C lowering in hyperlipidemic patients," Atherosclerosis, vol. 225, Issue 2, Dec. 2012, pp. 388-396.
Tirona, R.G., et al., "Polymorphisms in OATP-C: identification of multiple allelic variants associated with altered transport activity among European- and African-Americans," J Biol Chem, 2001, pp. 35669-35675, vol. 276.
Tobert, "Lovastatin and Beyond: The History of the HMG-CoA Reductase Inhibitors," Nat. Rev. Drug Discov., 2(7): 517-526 (2003).
Tyburczy et al., "Evaluation of low trans-fat edible oils by attenuated total reflection-Fourier transform infrared spectroscopy and gas chromatography: a comparison of analytical approaches." Analytical and bioanalytical chemistry 404.3 (2012): 809-819.
United Kingdom Search Report issued in application No. GB0803833.3 dated Jun. 27, 2008.
Uusitupa MIJ et al, Lathosterol and Other Noncholesterol Sterols During Treatment of Hypercholesterolemia With Lovastatin Alone and With Cholestyramine or Guar Gum, Arterioscler Thromb 12: 807-813, 1992.
van Himbergen TM, Matthan NR, Resteghini NA, et al. Comparison of the effects of maximal dose atorvastatin and rosuvastatin therapy on cholesterol synthesis and absorption markers. J Lipid Res 2009;50:730-9.
Vanhanen H, Miettinen TA. Pravastatin and lovastatin similarly reduce serum cholesterol and its precursor levels in familial hypercholesterolaemia. Eur J Clin Pharmacol 1992;42:127-30.
Vladutiu, et al., "Genetic risk factors associated with lipid-lowering drug-induced myopathies, Muscle Nerve," 2006, pp. 153-162, vol. 34.
Warnick et al., Clinical Chemistry Sep. 2001 vol. 47 No. 9 1579-1596.
Wellcome Trust Case Control Consortium, "Genome-wide association study of 14,000 cases of seven common diseases and 3,000 shared controls," Nature, 2007, pp. 661-678, vol. 447.
Weng TC, Yang YH, Lin SJ, Tai SH. A systematic review and meta-analysis on the therapeutic equivalence of statins. J Clin Pharm Ther 2010;35:139-51.
Wilson, P. W. F., et al., The Framingham Offspring Study, "Prediction of Incident Diabetes Mellitus in Middle-aged Adults," (2007) Arch Intern Med. 167(10):1068-1074.
Xu et al., "Organic anion transporting polypeptide-1B1 haplotypes in Chinese patients," Acta Pharmacologica Sinica, vol. 28, No. 10, pp. 1693-1697, Oct. 28, 2007.
Zocor datasheet, 2007.httD://www.emc.medicines.ora.uk/emc/assets/c/htmllDisDlavDoc.asD?DocumentID=120.
Zuccaro et al.t "Tolerability of statins is not linked to CYP450 polymorphisms, but reduced CYP2D6 metabolism improves cholesteraemic response to simvastatin and fluvastatin," Pharmacological Research, vol. 55, pp. 310-317, 2007.
Anderson, 2010, The Clinical Plasma Proteome: A Survey of Clinical Assays for Proteins in Plasma and Serum, Clinica Chemistry 56(2):177-185.
Brambilla et al., 2011, Normal Fasting Plasma Glucose and Risk of Type 2 Diabetes, Diabetes Care 34:1372-1374.
Cruz et al., 2004, Low Adiponectin Levels Predict Type 2 Diabetes in Mexican Children, Diabetes Care 27(6):1451-1453.
Degn et al., 2004, One Week's Treatment With the Long-Acting Glucagon-Like Peptide 1 Derivative Liraglutide (NN2211) Markedly Improves 24-h Glycemia and-and-Cell Function and Reduces Endogenous Glucose Release in Patients with Type 2 Diabetes, Diabetes 53:1187-1194.
Eddy et al., 2003, A trial-validated model of diabetes, Diabetes Care 26(11):3093-3101.
Eddy et al., 2003, Validation of the Archimedes Diabetes Model, Diabetes Care 26(11):3102-3110.
Fumeron et al., 2004, Adiponectin Gene Polymorphisms and Adiponectin Levels Are Independently Associated With the Development of Hyperglycemia During a 3-Year Period; The Epidemiologic Data on the Insulin Resistance Syndrome Prospective Study, Diabetes 53:1150-1157.
Harder et al., 2004, The Effect of Liraglutide, a Long-Acting Glucagon-Like Peptide 1 Derivative, on Glycemic Control, Body Composition, and 24-h Energy Expenditure in Patients; With Type 2 Diabetes, Diabetes Care 27(8):1915-1921.
Kaput et al., 2004, Nutritional genomics: the next frontier in the postgenomic era, Physiol Genomics 16:166-177.
Kaput et al., 2007, Application of nutrigenomic concepts to Type 2 diabetes mellitus, Nutrition, Metabolism & Cardiovascular Diseases 17:89-103.
Kaput, 2004, Diet-Disease Gene Interactions, Nutrition 20:26-31.
Krakoff et al., 2003, Inflammatory Markers, Adiponectin, and Risk of Type 2 Diabetes in the Pima Indian, Diabetes Care 26(6):1745-1751.
Lindstrom et al., 2003, The Diabetes Risk Score, Diabetes Care 26(3):725-731.
Lyssenko et al., 2005, Genetic Prediction of Future Type 2 Diabetes, PLoS Medicine 2(12):e345.
Madsbad et al., 2004, Improved Glycemic Control With No Weight Increase in Patients With Type 2 Diabetes After Once-Daily Treatment With the Long-Acting Glucagon-Like Peptide 1 Analog Liraglutide (NN2211), Diabetes Care 27(6):1335-1342.
Patent Examination Report No. 1 dated Jun. 11, 2014 for Patent Application No. AU 2011/261480.
Pradhan et al., 2001, C-Reactive Protein, Interleukin 6, and Risk of Developing Type 2 Diabetes Mellitus, JAMA 286(3):327-334.
Programme for the Prevention of Type 2 Diabetes in Finland, Finnish Diabetes Association, 2003-2010, Published in 2003.
Ravussin, 2002, Adiponectin enhances insulin action by decreasing ectopic fat deposition, The Pharmacogenomics Journal 2:4-7.
Spranger et al., 2003, Adiponectin and protection against type 2 diabetes mellitus, Lancet 361:226-228.
Studs et al., 2003, GLP-1 derivative liraglutide in rats with b-cell deficiencies: influence of metabolic state on b-cell mass dynamics, British Journal of Pharmacology 140:123-132.
Wilson et al., 2007, Prediction of Incident Diabetes Mellitus in Middle-aged Adults, Arch Intern Med 167:1068-1074.
International Search Report and Written Opinion for PCT/US2014/048022, with an International filing date of Jul. 24, 2014, dated Feb. 18, 2015, (17 pages).
Miettinen et al., 2000, Noncholesterol Sterols and Cholesterol Lowering by Long-Term Simvastatin Treatment in Coronary Patients: Relation to Basal Serum Cholestanol, Arteriosclerosis, Thrombosis, and Vascular Biology 20(3):1340-1346.
Thompson et al., 2002, Why some patients respond poorly to statins and how this might be remedied, European Heart Journal 23(3):200-206.
Thongtang et al, 2012, Effects of ezetimibe added to statin therapy on markers of cholesterol absorption and synthesis and LCL-C

(56) References Cited

OTHER PUBLICATIONS lowering in hyperlipidemic patients, Atherosclerosis 225(2):388:396.

* cited by examiner

METHODS FOR DETERMINING LDL CHOLESTEROL TREATMENT

REFERENCE TO RELATED APPLICATIONS

The present application is a continuation of U.S. non-provisional application Ser. No. 13/658,387, filed Oct. 23, 2012, now abandoned, which is a continuation of U.S. non-provisional application Ser. No. 12/472,351, filed on May 26, 2009 now abandoned, which claims the benefit of and priority to U.S. provisional patent applications having Ser. Nos. 61/056,163, filed on May 27, 2008, and 61/084,909, filed on Jul. 30, 2008. Each of the above-referenced applications is incorporated by reference.

TECHNICAL FIELD

The present invention relates generally to cardiovascular disease (CVD) risk assessment, diagnosis and treatment thereof. Specifically, the present invention pertains to a diagnosis and personalized treatment solution based on results from testing utilizing an extended CVD risk assay panel that measures the combination of traditional risk factors and new important risk markers, and analysis of said results via a CVD diagnosis and treatment protocol algorithm in order to assess CVD risk, evaluate efficacy of drug therapy, and optimize therapy.

BACKGROUND

Cardiovascular disease, which includes coronary heart disease (CHD) and stroke, is the leading cause of death and disability in developed countries of the world. CVD is caused by clogging of arteries. Major accepted risk factors for CVD include age, gender, hypertension, smoking, diabetes, elevated blood low density lipoprotein cholesterol (LDL-C), and decreased blood high density lipoprotein cholesterol (HDL-C).

In order to assess CVD risk, an assay panel is utilized for testing an individual's risk factors. A typical risk assessment screening test includes measuring fasting levels of total cholesterol (TC), triglycerides (TG), HDL-C, calculated LDL-C, hemoglobin A1c, and glucose. However, such a risk assessment panel is limited to traditional risk factors and does not provide a complete assessment of CVD risk, or ways to optimize treatment.

There are other tests for general metabolic factors of kidney, liver, muscle and thyroid function that are often not performed. These include blood urea nitrogen or BUN, creatinine, BUN/creatinine ratio, albumin, globulin, albumin/globulin ratio, alkaline phosphatase, liver enzymes AST and ALT, creatine kinase (CK), thyroid stimulating hormone (TSH), glomerular filtration rate (GFR), calcium, total protein, total bilirubin, sodium, potassium, chloride, carbon dioxide and uric acid; however, these tests are not always consistently used, despite their importance in ruling out secondary causes of lipid abnormalities.

There are other tests for heart disease risk, such as testing for levels of non-HDL cholesterol, and very low density lipoprotein cholesterol (VLDL-C), and the total cholesterol/HDL cholesterol ratio; however, these test are not consistently used in CVD risk assessment.

In addition there are specialized tests for CVD risk which include testing for levels of direct LDL cholesterol, small dense LDL cholesterol (sdLDL-C), lipoprotein (a) or Lp(a), apolipoprotein A-I (apoA-I), apolipoprotein B (apoB), fibrinogen, and homocysteine.

There are specialized testing for C-reactive protein (CRP with a highly sensitive test or hsCRP), lipoprotein associated phospholipase A2 (LpPLA2), N-terminal pro-brain natriuretic peptide (NT-proBNP), insulin, adiponectin, and glycosylated hemoglobin (HbA1C); however, they are not widely or consistently used in CVD risk assessment.

There are tests for plasma sterols, such as lathosterol, desmosterol, beta sitosterol, campesterol, and cholestanol; however, they are not widely or consistently used in CVD risk assessment.

In addition, genotyping of apolipoprotein E and Factor V Leiden provides valuable information about CVD and dementia risk, as well as risk of clot formation, but it is generally not utilized in CVD risk assessment.

Lipoproteins in serum or plasma are complexes of various lipids and proteins. The major lipoproteins based on ultracentrifugal separation are chylomicrons (CM), very low density lipoproteins (VLDL), low density lipoproteins (LDL), and high density lipoproteins (HDL). These lipoproteins can also be fractionated by size, protein components, electrophoretic mobility, or any combination of these. If plasma is subjected to two separation methods, the major lipoprotein classes can further be separated into subclasses. These subclasses differ from each other in size, charge, chemical composition, and patho-physiologic importance.

The ultracentrifugal (UC) method separates lipoproteins based on their respective specific flotation rate (density) into HDL, LDL, VLDL, and CM, in decreasing density, respectively. However, the UC method is very labor intensive, requires a specialized laboratory, and is very expensive. Moreover, the high separating force (100,000 times of normal gravity) used in this method affects the integrity of the lipoprotein particles, therefore, the UC method produces a significant amount of artifacts (in vitro altered lipoproteins) that affect the result. In addition, even finer fractionation of the sample is necessary for relating fractions to diseases, but the additional fractionation step increases the production of artifacts. For these reasons, separation of plasma or serum lipoproteins by ultracentrifugation is neither feasible nor ideal for clinical diagnostic evaluation of plasma lipoproteins and cardiovascular disease (CVD) risk.

Size exclusion separation of HDL, as with fast low pressure liquid chromatography (FPLC), has no adequate resolution, needs a large quantity of plasma, and produces artifacts due to the excessive dilution of the plasma. Magnetic nuclear resonance (NMR) is another characterization technique that is widely used, primarily because of its speed; however, it is unclear how to interpret NMR signal data or what these data represent. One-dimensional non-denaturing gel electrophoresis is also used for characterizing lipoproteins, such as HDL and LDL. With this method, lipoproteins are separated only by size. With this method, separation between the preβ-mobility and α-mobility HDL particles is not achievable. Thus, this method does not allow for the accurate assessment of α-1 HDL, preβ-2, or preβ-1 HDL, all of which are important particles for CVD risk assessment.

HDL can protect against atherosclerosis in several ways. The most cited HDL function to protect against atherosclerosis is its participation in reverse cholesterol transport. During this process, HDL removes cholesterol from macrophages in the vessel wall, preventing the transformation of macrophages into foam cells, eventually preventing the build-up of fatty streaks and plaque in the vessel wall. The cholesterol that originated in the macrophages is then carried by HDL to the liver for ultimate excretion into the bile.

HDL is also an anti-oxidant and anti-inflammatory agent. Oxidative stress can cause inflammation in the vessel wall.

The protein and lipid components of HDL can prevent LDL oxidation. This is a very important function because oxidized LDL is the major carrier of cholesterol to macrophages present in the vessel wall. Moreover, HDL has anti-inflammatory functions and participates in the immune response.

The different HDL particles have different pathophysiological relevance. The many different functions of HDL are not distributed evenly among the various HDL subclasses. The best illustration of this is that cells have several ways to remove excess cholesterol. The different HDL particles specifically interact with the different pathways depending on cell type, the expressed receptor protein type on the surface of the cell, and cellular cholesterol content. Also, the different HDL particles participate differently in the anti-oxidation and anti-inflammation processes based on the lipid and protein composition of the HDL particles.

Data from HDL- and CVD-related population-based studies reveal the following:

For every 1 mg increase in HDL cholesterol, there is a 2-3% reduction in CVD risk. ["High-density Lipoprotein Cholesterol and Cardiovascular Disease. Four Prospective American Studies.", Gordon, D. J. et. al., *Circulation*, 1989, January; 79(1):8-15].

In the Framingham Offspring Study, in men free of CHD (n=1277) and men with CHD (n=169), for every 1 mg/dl increase in α-1 HDL there was a 26% decrease in risk of CHD (probability ("p")<0.001), and HDL particles were superior to HDL-C values in predicting prevalence of CHD. ["High-density Lipoprotein Subpopulation Profile and Coronary Heart Disease Prevalence in Male Participants of the Framingham Offspring Study", Asztalos, B. F., et. al., *Arterioscler Thromb Vasc Biol.* 2004, November; 24(11):2181-7. Epub 2004 Sep. 23].

Patients with CHD have lower HDL-C due to decreases in the large cholesterol-rich α-1 HDL (−39%) and increases in the small lipid-poor alpha α-3 HDL (+29%) and pre-β1 HDL (+16%) as compared to age- and gender-matched controls. ["Distribution of ApoA-I-containing HDL Subpopulations in Patients with Coronary Heart Disease", Asztalos, B. F., et. al., *Arterioscler Thromb Vasc Biol.*, 2000, December; 20(12):2670-6; and "High-density Lipoprotein Subpopulation Profile and Coronary Heart Disease Prevalence in Male participants of the Framingham Offspring Study", as cited above].

In the Veterans Affairs HDL Intervention Study (VA-HIT), low levels of α-1 and α-2 HDL predicted recurrent CHD events (n=398) versus no recurrence (n=1097) in men selected for low HDL C (less than 40 mg/dl and presence of CHD. Low α-1 HDL was the most significant parameter predicting recurrence (p<0.001). ["Value of High-Density Lipoprotein (HDL) Subpopulations in Predicting Recurrent Cardiovascular Events in the Veterans Affairs HDL Intervention Trial", Asztalos, B. F., et. al., *Arterioscler Thromb Vasc Biol.*, 2005, October; 25(10):2185-2191].

Two-dimensional gel electropheresis is a separation method, based on the combination of two principles of electrophoretic separation (in the first dimension, particles are separated by charge and in the second dimension by size) that is very useful for reproducibly separating HDL particles with high resolution. The method is quantitative by utilization of protein immuno-localization and image-analysis. As a result of employing this two-dimensional HDL separation method, different HDL particles have been associated with CVD risk in population-based cross-sectional studies. The two-dimensional gel electrophoresis technology is also useful in the diagnosis of the homozygous and heterozygous state for rare inherited HDL disorders, such as apoA-I/C-III/A-IV, apoA-I/C-III deficiency, isolated apoA-I deficiency, ABCA1 deficiency, LCAT deficiency, SRB1 deficiency, CETP deficiency, lipoprotein lipase deficiency, hepatic lipase deficiency, and endothelial lipase deficiency. Based on the scans generated using this technique, it has become possible to differentiate among the various HDL particles; this allows for very precise evaluation of the severity of CVD-risk. Patients who are carriers of one normal and one damaged gene (referred to as heterozygotes) of the above list also have reduced levels of HDL and premature CVD. Patients who are carriers of two damaged genes (referred to as homozygotes) of the above list generally have a very high risk for premature CHD. Patients with ABCA1 mutations have only small pre-β1 HDL particles with hypercatabolism of apoA-I and have premature CHD. Patients affected with apoA-I deficiency have no HDL and have strikingly premature CHD. Whereas, patients affected with LCAT deficiency have only preβ-1 and α-4 HDL particles, and are at moderate to high risk for CVD. Different mutations in the cholesterol ester transfer protein (CETP) can cause either increased or decreased CETP activity, resulting in different changes in HDL particles. High CETP activity results in low levels of large α-1 and high levels of the small preβ-1 HDL particles. High CETP activity is associated with significant increased risk for CVD. Low CETP activity, which may be due to mutations in the gene encoding CETP or to effects of various drugs, causes high levels of α-1 HDL and low levels of preβ-1 HDL. This HDL subpopulation profile (high α-1 and low preβ-1) is associated with protection against CVD. Various mutations in the genes encoding lipoprotein-, hepatic-, and secretory-phospholipases can also be detected and recognized by their specific HDL subpopulation profile using this method.

Most importantly, the HDL subpopulation profile can differentiate subjects with increased risk for CVD independent of the HDL-C level. This is very important, as some subjects or an entire ethnic group may have low HDL-C level without any history of elevated CVD risk due to the fact that these subjects have not only increased HDL catabolism, but also enhanced HDL function. These subjects have a normal HDL particle distribution. However, some subjects with high HDL-C may experience a CVD event due to low HDL catabolism or dysfunctional HDL as seen with a defective SRB1 function.

Similar to HDL, LDL can also be separated into particles having different sizes, most commonly separated into small dense (sd) LDL and large LDL particles. It is proven and widely accepted in the lipoprotein field that sdLDL-C is more atherogenic than large LDL-C. The most common method for separating LDL by size is electrophoresis. The quantification of different LDL fractions is based on lipid staining in the gel, followed by density scanning and integrating the area under the curve. The major disadvantages of this method are that it is labor and time consuming, and has poor resolution. A more recent method involves the use of a specific mixture of detergents for removing other lipoproteins, and then measuring cholesterol only in small dense LDL or sdLDL. This method is adaptable to high throughput automated analyzers, and it has been standardized.

Risk for CVD is significantly higher in subjects with impaired glucose homeostasis. Risk for CVD among type 2 diabetic patients is as high as the risk among subjects with elevated LDL-C level. There are several ways to determine glucose homeostasis including the measurement of fasting and post-prandial blood glucose levels, insulin levels, and hemoglobin-A1c (HbA1c) determinations. Currently, HbA1c is the most commonly used test to determine the severity of diabetes. The method needs red blood cells and fresh samples. Because the in-vivo half-life time of hemoglobin is about two to three months, measuring the amount of glucose attached to hemoglobin or HbA1c has been shown to be an excellent measure of long-term (8-12 weeks) blood glucose control. However, doctors who treat patients with CVD usually look for a shorter time period to determine whether the medications they prescribe affect diabetes. Moreover, there is not a wide range of values in the normal population. There is a way to measure shorter term changes in glucose homeostasis, namely by measuring glycated albumin (GA) as the percentile of plasma total albumin, which represents the glycation status over the past two to four weeks versus the three month period of HbA1c. This measurement is easy; utilizes plasma samples, and can be measured from stored (frozen) samples. Further, its value correlates well with HbA1c values, and due to the larger dynamic range of GA % measurement, subjects without known diabetes can be characterized more accurately with regard to their risk of developing diabetes and CVD. GA % measurement can also facilitate the diagnosis of pre-diabetes status.

Cardiovascular disease is considered both a lipid storage and an inflammatory disease. One of the inflammatory markers that have been shown to be an independent marker of CVD is C-reactive protein (CRP). CVD patients have increased CRP level. CRP has been a very well studied CVD-risk factor in the last couple of years. CRP is measured in plasma using a high sensitivity CRP assay kit. Recently, it has been found that CRP has several molecular forms (CRPmf) in human plasma. These forms differ in electrophoretic mobility and size, as assessed by polyacrylamide gel electrophoresis and immuno-localization under special conditions. The concentrations of the smallest molecular form (CRP mf4), or the ratio of this small CRP mf4 to the largest one (CRP mf1) is positively associated with fat cell mass (obesity) and with the presence of CVD.

Adiponectin is a protein hormone that modulates a number of metabolic processes, including glucose regulation and fatty acid catabolism. Adiponectin is exclusively secreted by adipose tissue into the bloodstream and is very abundant in plasma relative to many other hormones. Levels of the hormone are inversely correlated with body fat percentage in adults. The hormone plays a role in the suppression of the metabolic derangements that may result in type 2 diabetes, obesity, atherosclerosis and non-alcoholic fatty liver disease.

Despite the evident need for a better predictor of CVD, the market lacks a diagnostic solution consisting of a complete test panel for screening of an individual's CVD risk and a process for an accurate and individualized diagnosis and treatment plan derived from the results of the screening tests in order to optimize therapy and decrease CVD risk, especially in those patients who already have established CVD.

SUMMARY OF THE INVENTION

Diagnostic screening panels for assessing cardiovascular risk exist; however, these tests are limited in the breadth of CVD risk factors.

In view of the above, there is a need for a diagnostic solution that will provide more complete CVD-risk assessment, and thereby assure a more accurate and individualized treatment plan. Further, there is a need for an individualized treatment protocol utilizing recent developments in HDL particle subfractionation.

It is, therefore, an aspect of the present invention to provide an extended CVD-risk panel that tests and/or measures the combination of traditional risk factors and new important risk markers.

It is another aspect of the present invention to provide a means for obtaining more detailed information about the disturbance in lipoprotein and glucose metabolisms and inflammatory status of an individual.

It is another aspect of the present invention to provide a means for monitoring drug effectiveness with greater accuracy and speed than traditional testing methods in the treatment of cardiovascular disease.

It is another aspect of the present invention to provide a CVD protocol algorithm for the analysis of the results obtained from the extended risk panel testing, in order to facilitate personalized treatment options for a patient.

It is another aspect of the present invention to provide a treatment plan for the personalized treatment of a cardiovascular disease or management of cardiovascular risk in an individual.

The present invention pertains to a comprehensive diagnostic screening solution for assessing CVD risk. This novel diagnostic solution comprises an extended CVD-risk panel for testing of traditional risk factors in combination with new and emerging tests. The extended CVD risk assessment panel tests for the following: general metabolic factors of blood urea nitrogen or BUN, creatinine, BUN/creatinine ratio, glomerular filtration rate (GFR), calcium, alkaline phosphatase, liver enzymes AST and ALT, creatine kinase (CK), thyroid stimulating hormone (TSH), sodium, potassium, chloride, carbon dioxide, and uric acid; specialized heart disease factors in addition to total cholesterol, total triglyceride, high density lipoprotein (HDL) cholesterol, calculated low density lipoprotein (LDL) cholesterol, non-HDL cholesterol, very low density lipoprotein (VLDL) cholesterol, and total cholesterol/HDL cholesterol ratio; as well as specialized lipid factors of direct LDL cholesterol, small dense LDL cholesterol, apolipoprotein apoA-I and apoB, lipoprotein (a) or Lp(a), highly sensitive C-reactive protein (hsCRP) and CRP molecular forms (CRPmf), lipoprotein associated phospholipase A2 (LpPLA2), fibrinogen, glycated albumin, globulin, albumin/globulin ratio, glycosylated hemoglobin, total bilirubin, adiponectin, homocysteine, and insulin; HDL subpopulations (by two-dimensional gel electropheresis) of $\alpha$-1 HDL, $\alpha$-2 HDL, $\alpha$-3 HDL, $\alpha$-4 HDL, and pre$\beta$-1 HDL particles; markers of cholesterol synthesis (plasma levels of lathosterol and desmosterol); markers of cholesterol absorption (plasma levels of beta sitosterol, campesterol, and cholestanol); and other specialized testing pertaining to apolipoprotein E and Factor V Leiden genotyping, and NT-proBNP or N-terminal pro-brain natriuretic peptide.

This extended CVD-risk panel yields more detailed information about the disturbance in lipoprotein and glucose metabolisms and inflammatory status in an individual, and about the effectiveness of an applied medication to treat disorders of lipoprotein metabolism, inflammation, and glucose homeostasis, thereby leading to more personalized treatment.

The diagnostic solution of the present invention provides not only superior assessment of CVD risk prospectively, but also assessment of risk of recurrent CVD events in individuals who have already experienced CVD events. Further, the panel of CVD-risk markers may be selected so as to predict a change in risk for CVD, as well as to optimize treatment. The CVD risk panel comprises at least one test or measurement ("test or measurement" shall collectively be referred to as "tests"), depending on the particular marker, for each of the following markers: total cholesterol, total triglyceride, lipoprotein particles, apolipoproteins, diabetes and fat metabolism, plasma sterols, inflammatory markers, genetic testing, and secondary causes of high cholesterol; said tests for lipoprotein particles comprising at least one test for each of the following: direct high density lipoprotein cholesterol, HDL subparticle fractionation by two-dimensional gel electrophoresis, direct low density lipoprotein cholesterol, direct small dense LDL cholesterol, percentage of LDL cholesterol as small dense LDL cholesterol, lipoprotein (a), and non-HDL cholesterol and total cholesterol/ HDL cholesterol ratio; said test for markers of diabetes comprising at least one test for each of the following: insulin, albumin, glycosylated hemoglobin, and glycated albumin; said test for plasma sterols comprising at least one test for each of the following: lathosterol, desmosterol, campesterol, beta-sitosterol, and cholestanol; said test for inflammatory markers comprising at least one test for each of the following: C reactive protein and lipoprotein associated phospholipase A2; said test for genetic testing comprising at least one test for each of the following: apolipoprotein E genotype, and factor V Leiden genotype; and said test for secondary causes of high cholesterol comprising at least one test for each of the following: creatinine, blood urea nitrogen, creatine kinase, liver transaminases, alkaline phosphase, thyroid stimulating hormone, and uric acid. Each of the tests for each of the markers may be selected so as to predict present risk and a change in risk for CVD, as well as to optimize treatment.

The present invention also pertains to a method of personalized treatment of cardiovascular disease. CVD is a combined term for about 20 diseases currently known. The CVD risk assessment panel of the present invention enables the determination of which disease of the group of diseases that a particular patient has or presents a risk therefor. For many of these diseases, the particular biological or physiological mechanism of dysfunction is known. Further, particular useful and beneficial therapies are known for many of these dysfunctions. Therapies in this respect can be personalized with lifestyle therapy (modified diet low in cholesterol, saturated fat, trans fat, and sugars, and increased in fiber and essential fatty acids, as well as increased physical activity), nutritional supplements (such as omega 3 fatty acids, and coenzyme Q10), and particular drug(s), such as effective statins, cholesterol absorption inhibitors, niacin products, fibrates, resins, and other medical therapies in development (including CETP inhibitors). Thus, the CVD risk assessment panel of the present invention allows the treating healthcare practitioner to determine the patient's particular disease dysfunction, and to propose an optimal personalized treatment plan for the patient.

The present invention comprises the performance of diagnostic analysis, utilizing the CVD diagnosis protocol algorithm of the present invention, to optimally assess the CVD risk of a patient, and facilitate the personalized treatment plan for an individual while monitoring drug effectiveness, with greater accuracy and speed than traditional testing methods for the treatment of cardiovascular disease or prevalent risk therefor.

The above summary of the present invention is not intended to describe each illustrated embodiment or every implementation of the present invention. The figures and the detailed description that follow particularly exemplify these embodiments.

BRIEF DESCRIPTION OF THE DRAWINGS

The invention may be more completely understood in consideration of the following detailed description of various embodiments of the invention in connection with the accompanying drawings, in which:

In FIG. 1A and FIG. 1B, HDL particles separated from whole plasma by electrophoresis are shown in the vertical dimension for size (from large on top to small on the bottom of the gel), and in the horizontal dimension by charge into pre-β, α, and pre-α mobility. Subsequently, particles are analyzed for their apoA-I content by immunoblotting with specific antibodies and then performing quantitative image analysis. The HDL particle profile of a healthy control subject is shown on the left (FIG. 1A) and a patient with CVD is shown in the middle (FIG. 1B). These figures show that CVD patients have less α-1 HDL and α-2 HDL (which are the most protective particles), and more pre-β1 HDL than healthy subjects (FIG. 1A), and that a high concentration of pre-β1 HDL is associated with higher risk. The "*" indicates the position of albumin, a 67 kD plasma protein, that marks the α-front. The scan of the a region, as shown at the bottom portion of FIG. 1A, represents the integration of the α-mobility HDL particles. This scan is used to define the positions of the individual α mobility particles. The concentration of apoA-I in all HDL particles is then determined via image analysis. The illustration in FIG. 1C represents the positions of all apoA-I containing HDL particles.

FIG. 4A is a diagram generally depicting the method of performing a diagnosis analysis utilizing the CVD diagnosis and treatment protocol algorithm, with the healthcare practitioner devising the treatment plan for the patient, according to one embodiment of the present invention. FIG. 4B is a diagram generally depicting the method of performing a diagnosis and treatment analysis utilizing the CVD diagnosis and treatment protocol algorithm, according to one embodiment of the present invention.

Figures 1A, 1B, 1C:
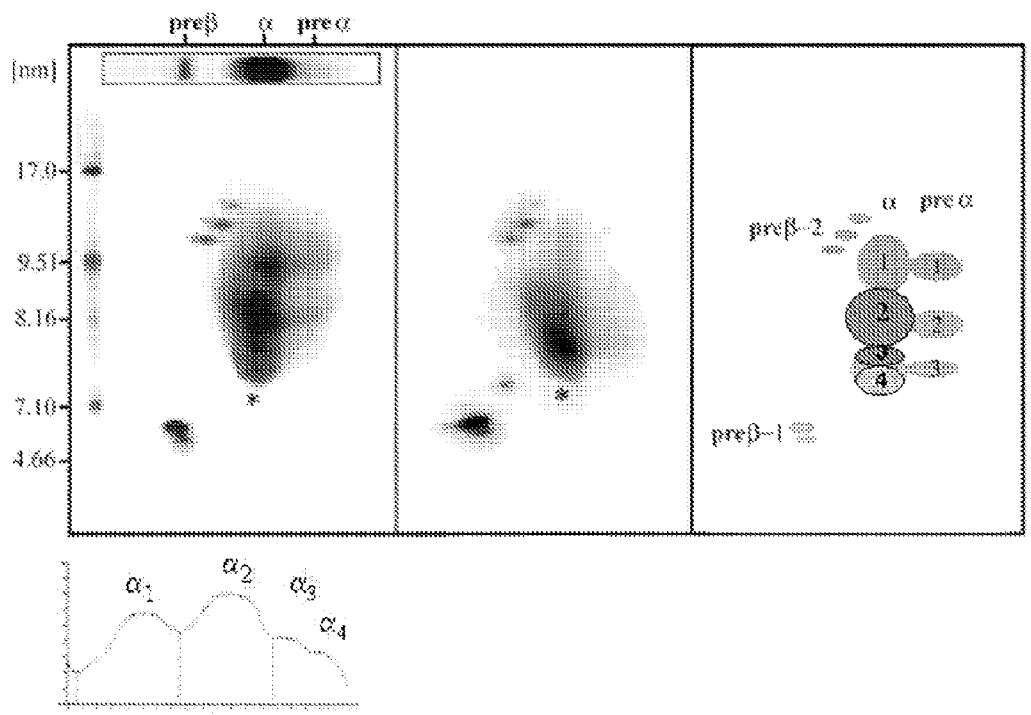
FIG. 1A-FIG. 1C illustrate typical results of the HDL subpopulation analysis assessed by two-dimensional gel electrophoresis, immuno-localization, and image-analysis, as described in prior art. These figures serve to demonstrate the effectiveness of this testing method as applied to the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention pertains to a diagnostic solution comprising an extended risk assessment panel for cardiovascular disease. The present invention also pertains to a personalized treatment solution for the treatment of CVD in an individual.

1. Definitions

The term "adiponectin", as used herein, refers to a protein hormone made in a person's fat, but only in subcutaneous fat, and not in visceral fat (the fat around a person's middle portion that increases his or her waist size). High levels of adiponectin indicate protection from heart disease, while low levels increase CVD risk in overweight or obese subjects.

The term "alkaline phosphatase", as used herein, refers to a measure of liver function and bile flow, as well as bone status. An alkaline phosphatase value between 33 U/L and 130 U/L is considered normal; whereas, an elevated value may indicate obstruction of bile flow, excess breakdown of bone, or malignancy.

The term "α-1 HDL particle" or "α-1", as used herein, refers to the apoA-I concentration in the HDL particles with a median size of about 11.0 nm. It is one of the most important HDL particles for predicting heart disease. This large particle delivers cholesterol to the liver. This HDL particle is large and lipid-rich; it contains 6 molecules of apoA-I, a large amount of free cholesterol and phospholipids (PL) on the surface, and cholesterol ester and TG in the core. This is the particle that interacts with scavenger receptor B1 (SRB1) in the liver and dumps cholesterol into the bile. A decreased level marks an inadequate HDL metabolism and is associated with increased risk for CVD. A value below 12.0 mg/dl is associated with increased heart disease risk in men and a value below 18.0 mg/dl is associated with increased heart disease risk in women, while a value between 12.0 mg/dl and 17.0 mg/dl in men and a value between 18.0 mg/dl and 28.0 mg/dl in women is considered borderline. A value above 17.0 mg/dl in men and above 28.0 mg/dl in women is considered normal.

The term "α-2 HDL particle" or "α-2", as used herein, refers to the apoA-I concentration in the HDL particles having a median size of about 9.20 nm. It is one of the most important HDL particles for predicting heart disease. This HDL particle is quite large and delivers cholesterol to the liver. A value below 38.0 mg/dl is associated with increased heart disease risk in men and a value below 45 mg/dl is associated with increased heart disease risk in women, while a value is between 38.0 mg/dl and 40.0 mg/dl in men, and between 45.0 mg/dl and 52.0 mg/dl in women is considered borderline. A value above 40.0 mg/dl in men and above 52.0 mg/dl in women is considered optimal.

The term "α-3 HDL particle" or "α-3", as used herein, refers to the apoA-I concentration in the HDL particles having a median size of about 8.00 nm. There is no established optimal or normal level for α-3; however, a ratio of α-1 to α-3 of less than 0.3 is an indication of abnormal HDL metabolism and increased risk for CVD.

The term "α-4 HDL particle" or "α-4", as used herein, refers to the apoA-I concentration in the HDL particles having a median size of about 7.42 nm. There is no established optimal or normal level for α-4; however, a ratio of α-1 to α-4 of less than 0.6 is an indication of abnormal HDL metabolism and increased risk for CVD.

The term "albumin", as used herein, refers to a measure of protein metabolism and nutritional status. An albumin value of 3.5-4.9 g/dl is considered normal; a decreased value may indicate malnutrition or chronic illness.

The term "apolipoprotein A-I" or "apoA-I", as used herein, refers to the measure of the most abundant protein component of HDL having a 28 kilo Daltons (KD) molecular weight. ApoA-I is an essential component of HDL; low level of apoA-I is associated with low level of HDL-C and high risk for CVD.

The term "apoA-I Fractional Catabolic Rate", as used herein, refers to the rate of degradation of apoA-I.

The term "apolipoprotein B" or "apoB", as used herein, refers to a measure of the fundamental protein component of VLDL and LDL having a 500 KD molecular weight. Apolipoprotein B has been reported to be a better predictor of heart disease than LDL cholesterol. An apoB value of above 120 mg/dl indicates high risk, a value between 60 mg/dl and 120 mg/dl is considered borderline, and a value below 60 mg/dl is considered to be optimal. A high value is associated with an increased risk for CVD.

The term "apolipoprotein E genotyping" or "apoE", as used herein, refers to testing of DNA for determining one of the genetic causes of heart disease risk. There are three different forms of apoE in human plasma: apoE2, apoE3 and apoE4. The normal apoE genotype is apoE3/3, while the apoE2/2 genotype is associated with an increased risk of elevated triglyceride values, and the apoE4/4 and apo4/3 genotypes are associated with increased LDL-C, increased cholesterol absorption, and increased risk of CVD and dementia.

The term "ALT", as used herein, refers to a measure of liver function. Normal ALT value is between 6 U/L and 40 U/L; a value of above 120 U/L is definitely abnormal and indicates either a fatty liver, liver disease, or a side effect of a medication (such as a statin).

The term "AST", as used herein, refers to a measure of liver function. An AST value between 10 mg/dl and 35 mg/dl U/L is considered normal; whereas, a value above 105 mg/dl is definitely abnormal and indicates a fatty liver, liver disease, or a side effect of a medication (e.g., a statin).

The term "beta sitosterol", as used herein, refers to a marker of cholesterol absorption. A beta sitosterol value above 250 in both men and women is considered very high and is diagnostic of beta-sitosterolemia or phytosterolemia associated with premature heart disease, while a value above 150 in women and above 160 in men is considered high, and a value between 130 and 150 in women and between 150 and 160 in men is considered borderline. A value below 130 in women and below 150 in men is considered optimal. [Provided in units relative to total plasma cholesterol as 'mmol×10$^2$/mol of cholesterol'.]

The term "blood urea nitrogen" or "BUN", as used herein, refers to a measure of kidney function. A BUN value of 25 mg/dL or below is considered normal, while an elevated value may indicate decreased kidney function.

The term "calculated low density lipoprotein cholesterol", "low density lipoprotein cholesterol" or "LDL-C", as used herein, refers to the level of the cholesterol in the particle that causes heart disease. This value is calculated by subtracting the sum of HDL cholesterol and triglyceride/5 from total cholesterol. The calculation is not valid if the subject is not fasting or if the triglyceride value is above 400 mg/dl. An LDL-C value above 160 mg/dl is considered very high, whereas a value between 130 mg/dl and 160 mg/dl is considered high, a value between 100 mg/dl and 130 mg/dl is considered borderline, and a value below 100 mg/dl is considered optimal. For heart disease patients, an ideal LDL cholesterol level is below 70 mg/dl. A high value is associated with an increased risk of CVD.

The term "campesterol", as used herein, refers to a marker of cholesterol absorption. A value greater than 250 in both men and women is considered very high, a value greater than 200 in women and greater than 220 in men is considered high, and a value between 180 and 200 in women and between 200 and 220 in men is considered borderline, while a value less than 180 in women and less than 200 in men is considered optimal. [Provided in units relative to total plasma cholesterol as 'mmol×$10^2$/mol of cholesterol'.]

The term "cholestanol", as used herein, refers to a marker of cholesterol absorption. A cholestanol value above 250 in both men and women is considered very high and is diagnostic of cerebrotendinous xanthomatosis associated with neurologic disease, a value above 140 in men and women is considered high, a value between 130 and 140 in men and women is considered borderline, while a value below 130 in both men and women is considered optimal. [Provided in units relative to total plasma cholesterol as 'mmol×$10^2$/mol of cholesterol'.]

The term "creatinine", as used herein, refers to a direct measure of kidney function. A creatinine value below 1.20 mg/dL is considered normal; whereas, an elevated value indicates decreased kidney function.

The term "creatinine kinase" or "CK", as used herein, refers to a muscle enzyme test. A creatinine kinase value between 0 and 165 U/L is considered normal; whereas, an elevated value, especially above 1650 U/L, indicates significant breakdown of muscle, either from heavy exercise or from a medication (rarely), such as a statin. If the patient has such an elevated value and experiences muscle aches and pains not clearly related to exercise, then the patient should stop taking the statin.

The term "desmosterol", as used herein, refers to a marker of cholesterol synthesis. A desmosterol value above 80 in women and above 75 in men is considered high, while a value between 70 and 80 in women and between 70 and 75 in men is considered borderline. A value below 70 in both men and women is considered optimal. [Provided in units relative to total plasma cholesterol as 'mmol×$10^2$/mol of cholesterol'.]

The term "direct LDL cholesterol", as used herein, refers to direct low density lipoprotein cholesterol. A direct LDL cholesterol value above 160 mg/dl is very high, while a value between 130 mg/L and 160 mg/dl is considered high, a value between 100 mg/dl and 130 mg/dl is considered borderline, and a value below 100 mg/dl is considered optimal. In heart disease patients, an ideal LDL cholesterol level is less than 70 mg/dl. A high value is associated with an increased risk of heart disease.

The term 'Factor V Leiden", as used herein, refers to a genetic variant in clotting factor V that causes increased risk for the development of clot formation in the veins of the legs, which can result in such clots moving to the lungs. This is a genetic test.

The term "glycated albumin", as used herein, refers to a test to determine the quantity of glucose attached to the albumin in a person's blood. It is a potent predictor of heart disease in the non-diabetic population, and a potent predictor of complications in those with diabetes. A value above 16.5% indicates the presence of diabetes mellitus.

The term "HDL subfractionation by two-dimensional gel electrophoresis", "two-dimensional gel electrophoresis", "two-dimensional HDL separation" or "HDL fingerprinting", as used herein, refers to a technology that measures different HDL particles by directly separating the particles by size and charge, and then measuring the amount of the protein A-I in each particle. It assesses how well a person's HDL particles are functioning in order to help remove cholesterol from the body. This test not only measures the small HDL particles that pick up cholesterol from the artery wall but also the large HDL particles that deliver cholesterol to the liver. These small HDL and large HDL particles help provide very precise information about a person's heart disease risk. Also, measuring these particles helps to determine how well a therapy with medication(s) is working in a patient.

The term "healthcare facility", as used herein, refers to a hospital, clinic, healthcare practitioner's facility, laboratory or medical testing or imaging facility, or the like.

The term "healthcare practitioner", as used herein, refers to a healthcare professional or a healthcare provider, such as a physician, a nurse practitioner, or a physician's assistant, who provides or manages the medical care of a patient. The healthcare practitioner is authorized to conduct the testing of the patient with the extended test panel disclosed herein, perform diagnosis analysis or diagnosis and treatment analysis via the diagnosis and treatment protocol algorithm disclosed herein, interpret the results of the diagnosis analysis, interpret the results of the diagnosis and treatment analysis, devise or modify an individualized treatment plan, monitor the efficacy of drug therapy, monitor the effectiveness of treatment plan, and manage the health care of a patient.

The term "high density lipoprotein cholesterol" or "HDL-C", as used herein, refers to the cholesterol measurement in plasma, after the removal of apoB-containing lipoproteins (VLDL and LDL particles). High levels of HDL cholesterol, above 60 mg/dl, protect against heart disease. A value between 40 mg/L and 60 mg/dl is considered borderline, while a low HDL cholesterol value, below 40 mg/dl in men and below 50 mg/dl in women, is associated with an increased risk of heart disease.

The term "highly sensitive C Reactive Protein" or "hsCRP" or "CRP", as used herein, refers to a measure of inflammation in a person's blood. A CRP value above 3.0 mg/L is considered high, a value between 2.0 mg/L and 3.0 mg/L is considered borderline, and a value of less than 2.0 mg/L is considered normal, while some authorities recommend maintaining CRP values below 1.0 mg/L. A high value is associated with an increased risk for CVD.

The term "highly sensitive C-reactive protein molecular form" or "CRPmf", as used herein, refers to a measure of specific CRP protein (complex) in a person's blood. CRP mf-1 is the largest form and CRP mf-4 is the smallest form of the major molecular forms of CRP. The presence of CRPmf-4 in plasma is associated with an increased CVD risk in obese and diabetic subjects.

The term "insulin", as used herein, refers to a very important hormone in a person's blood that regulates a person's blood glucose. A fasting insulin level above 20 microunits/ml ("mU/ml") is considered high, a value between 10 mU/ml and 20 mU/ml is considered borderline, and a value below 10 mU/ml is considered ideal. High values are associated with insulin resistance and an increased risk for CVD. A very low value, below 5 mU/ml, in the setting of diabetes is consistent with insulin deficiency and a need for insulin therapy.

The term "lab technician", as used herein, refers to an authorized person employed at a healthcare facility, and who may conduct the testing of a patient with the extended panel of the present invention. A lab technician may also be authorized to enter the results of the testing for the performance of the diagnosis analysis via the protocol algorithm of the present invention, and/or to perform said analysis.

The term "lathosterol", as used herein, refers to a marker of cholesterol production. A lathosterol value above 150 in women and above 135 in men is considered high, a value between 130 and 150 in women and between 120 and 135 in men is considered borderline, while values below 130 in women and below 120 in men are considered optimal, [Provided in units relative to total plasma cholesterol as 'mmol×$10^2$/mol of cholesterol'.]

The term "lipoprotein (a)" or "Lp(a)", as used herein, refers to an LDL particle with another protein (referred to as apo(a)) attached thereto. A high value of this particle can interfere with the process of breaking up clots in a person's arteries. An Lp(a) value above 30 mg/dl is considered high, while a borderline value is between 20 mg/dl and 30 mg/dl, and an optimal value is below 20 mg/dl. A high value is associated with an increased risk of heart disease.

The term "lipoprotein associated phospholipase A2" or "LpPLA2", as used herein, refers to a marker of inflammation. An LpPLA2 value above 235 ng/ml is considered high, while a value between 200 ng/ml and 235 ng/ml is considered borderline, and a value below 200 ng/ml is considered optimal. A high value is associated with an increased risk of heart disease.

The term "non-HDL cholesterol", as used herein, refers to a calculated value (total cholesterol minus HDL cholesterol). A non-HDL cholesterol value above 190 mg/dl is considered very high risk, while a value between 160 mg/dl and 190 mg/dl is considered high risk, and a value between 130 mg/dl and 160 mg/dl is considered borderline. A value below 130 mg/dl is considered optimal, with a value below 100 mg/dl being a target value for patients with heart disease. A high value is associated with an increased risk of heart disease.

The term "N-terminal pro-Brain natriuretic peptide" or "NT-proBNP", as used herein, refers to a marker of heart disease stress. High levels have been associated with an increased risk of mortality in patients with heart disease. An NT-proBN value above 450 pg/dl is considered high, while a value between 125 pg/ml and 450 pg/ml is considered borderline high, and a value below 125 pg/dl is considered optimal.

The term "patient" or "subject", as used herein, refers to a person or an individual who is at risk for or has already exhibited one or more aspects of a disease or, particularly cardiovascular disease or CVD.

The term "preβ-1 HDL particle", as used herein, refers to an important HDL particle for predicting heart disease. This HDL particle is quite small, contains 2 apoA-I and 16 phospholipid (PL) molecules. This is the particle that picks up cholesterol from the artery wall via the ABCA1 pathway. An increased level marks an inadequate HDL metabolism and is associated with an increased risk for CVD. A value above 20.0 mg/dl is associated with increased heart disease risk in both men and women, while a value between 15.0 mg/dl and 20.0 mg/dl in both men and women is considered borderline. A value below 15.0 mg/dl in both men and women is considered optimal.

The term "small dense LDL cholesterol" or "sdLDL-C", as used herein, refers to the cholesterol level in the LDL particles that confer the highest risk of heart disease. An sdLDL-C value above 40 mg/dl is considered high, while a value between 20 mg/dl and 40 mg/dl is considered borderline, and a value below 20 mg/dl is considered optimal. In heart disease patients, it is recommended that small dense LDL cholesterol level be maintained below 20 mg/dl. A high value is associated with an increased risk of heart disease.

The term "thyroid stimulating hormone" or "TSH", as used herein, refers to a sensitive measure of thyroid function. A thyroid stimulating hormone value between 0.5 micrograms/L and 5.5 micrograms/L is considered normal. A high value indicates an underactive thyroid gland and hypothyroidism, which causes fatigue, cold intolerance, dry skin, constipation, and an elevated blood cholesterol level, while a low value is due to an overactive thyroid gland, and can cause a rapid heart beat and even palpitations.

The term "total cholesterol", as used herein, refers to the sum of the cholesterol in all of the cholesterol carrying particles in a person's blood. A total cholesterol value above 240 mg/dl is considered high, while a value between 200 mg/dl and 240 mg/dl is considered borderline, and a value below 200 mg/dl is considered optimal. A high value is associated with an increased risk of heart disease.

The term "total cholesterol/HDL cholesterol ratio", as used herein, refers to a measure of heart disease risk. A value above 6.0 is considered very high risk, while a value between 5.0 and 6.0 is considered high risk, a value between 4.0 and 5.0 is considered borderline, and a value below 4.0 is considered optimal (recommended as a target by both the Canadian and European guidelines panel for heart disease patients). A high value is associated with an increased risk for CVD.

The term "triglyceride" or "TG", as used herein, refers to a fat in a person's blood. Very high levels of triglyceride, above 1000 mg/dl, increase the risk of pancreatitis, while a high value, above 150 mg/dl, is associated with an increased risk for CVD.

The term "uric acid", as used herein, refers to a substance in the bloodstream derived from the breakdown of protein. High level of uric acid, above 10.0 mg/dl, is associated with an increased risk for both gout and CVD, and can be a cause of gouty arthritis and kidney stones.

The term "very low density lipoprotein cholesterol" or "VLDL-C", as used herein, refers to a lipoprotein particle in fasting plasma. A VLDL-C value above 30 mg/dl is considered high, while a value below 30 mg/dl is considered optimal. A high value is associated with an increased risk for CVD.

It is to be understood that the singular forms of "a", "an", and "the", as used herein and in the appended claims, include plural reference unless the context clearly dictates otherwise.

2. Diagnostic Solution for Assessing Cardiovascular Disease Risk

The present invention provides an unique diagnostic solution, in that an extensive risk assessment panel provides information pertaining to the levels of certain important markers, as well as information pertaining to genetic testing and traditional risk factors; such knowledge facilitates a healthcare practitioner to optimize therapy with lifestyle modification and pharmacologic therapy in subjects with cardiovascular disease (e.g., heart disease, stroke), or individuals at high risk of developing these disorders.

2.1 the Extended Risk Assessment Panel

The diagnostic solution of the present invention comprises a rather comprehensive test panel for assessing CVD-risk beyond the traditional risk factors and tests. This solution provides a comprehensive CVD risk assessment by testing or measuring (collectively, "testing") for all of the following: the general metabolic factors, the specialized heart disease factors, the specialized lipid factors, the plasma sterols, the HDL subpopulations (by two-dimensional gel electrophoresis), the CRP molecular forms, and other specialized testing pertaining to apolipoprotein E genotyping, Factor V Leiden genotyping, NT-proBNP or N-terminal pro-brain natriuretic peptide, adiponectin, and glycated albumin. With the exception of genetic testing, which need only be performed once in a lifetime for a particular patient due to the nature of the test, such as at the time of initial assessment testing, the panel of tests may be performed multiple times for a given patient, for example, when a treating healthcare practitioner needs to assess the patient's current CVD risk, or assess the patient's response to therapy. Preferably, all tests are performed at each instance of testing of a patient; each of such instances of testing is referred to as "subsequent testing", as they are performed subsequent to the initial assessment testing.

The comprehensive nature of the risk assessment panel of the present invention does not mean that all tests are performed from the same sample from the patient or that the tests are all performed at the same time, although, all of the tests that must be performed for a given patient are preferably performed in close proximity in time so that the test results can be used in combination to comprehensively assess risk and perform diagnosis or diagnosis and treatment analysis. The "tests that must be performed for a given patient" means all of the tests for initial assessment, i.e., the first time that a treating healthcare practitioner orders such tests for the patient, and means only those tests that must be repeated for subsequent evaluations of that patient, such as the occasions when a treating healthcare practitioner needs to assess the patient's current CVD risk, or the patient's response to therapy. Certain test results can be re-utilized, without re-testing a patient (particularly genetic testing results; and possibly plasma sterol testing, depending on the patient), in combination with the repeated or subsequent test results, in the performance of the analysis that yields the current diagnosis or current diagnosis and treatment information for the subsequent testing time frame (as a patient's risk for CVD or response to therapy may change during any period of time).

In order to assess an individual's complete CVD-risk profile, the extended CVD-risk panel is utilized to specifically test for the following:

1. Total Cholesterol
2. Total Triglyceride
3. Lipoprotein Particles (Lipoproteins)
    3.1 Direct High Density Lipoprotein (HDL) Cholesterol
    3.2 HDL subpopulations (by Two-Dimensional Gel Electrophoresis)
    3.3 VLDL Cholesterol
    3.4 Direct Low Density Lipoprotein (LDL) Cholesterol
    3.5 Direct Small Dense LDL Cholesterol
    3.6 Percentage of LDL Cholesterol as Small Dense LDL Cholesterol
    3.7 Lipoprotein (a)
    3.8 Non-HDL Cholesterol and Total Cholesterol/HDL Cholesterol Ratio
4. Apolipoproteins
    4.1 Apolipoprotein A-I ("apoA-I")
    4.2 Apolipoprotein B ("apoB")
5. Markers of Diabetes and Fat Metabolism
    5.1 Insulin
    5.2 Albumin
    5.3 Glycated Albumin
    5.4 Glycosylated Hemoglobin
    5.5 Adiponectin
6. Plasma Sterol Analysis
    6.1 Lathosterol
    6.2 Desmosterol
    6.3 Campesterol
    6.4 Beta-sitosterol
    6.5 Cholestanol
7. Inflammatory Markers
    7.1 C-Reactive Protein (CRP)
    7.2 CRP molecular forms (CRPmf)
    7.3 Lipoprotein Associated Phospholipase A2 (Lp-PLA2)
8. Mortality Marker
    8.1 NT-Pro Brain Natriuretic Peptide
9. Genetic Testing
    9.1 Apolipoprotein E Genotype
    9.2 Factor V Leiden Genotype
10. Secondary Causes of High Cholesterol and Safety Testing
    10.1 Creatine Kinase
    10.2 Liver Transaminases (ALT, AST)
    10.3 Alkaline Phosphase
    10.4 Thyroid Stimulating Hormone
    10.5 Uric Acid
    10.6 Blood Urea Nitrogen
    10.7 Creatinine The results from all of these tests enable the treating healthcare practitioner to optimize therapy in patients with or without established CVD.

The solution of the present invention focuses on the above-listed tests as they pertain to factors that have great impact on CVD risk.

Levels of high density lipoprotein (HDL) greatly correlate with CVD risk. Thus, testing for and measuring HDL levels is an important aspect of assessing CVD risk. While measuring HDL levels via standard and other special lipid tests, such as for direct HDL cholesterol levels, provides valuable information, measuring HDL particle compositions, i.e., subfractions, provides a much more accurate and complete picture of how well HDL is functioning. The effects of many drugs on these subclasses are known, and thus knowing the level of an individual's HDL subclasses will lead to a more targeted and personalized treatment for patients.

HDL subpopulation analysis by two-dimensional gel electrophoresis involves separation of lipoproteins. HDL can be separated by electrophoretic mobility into preβ, α, and preα-mobility particles, and can be separated by size in the range of from about 6 nanometers to about 12 nanometers. Specifically, lipoproteins are fractionated primarily with respect o differences in their electrophoretic mobility and/or size. When lipoproteins are fractionated using the electrophoretic technique, they are separated into the fractions of preβ-mobility HDL, α-mobility HDL, and preα-mobility HDL. FIG. 1a-FIG. 1c serve to demonstrate the effectiveness, and thereby the suitability of use of this test as a part of the present invention. FIG. 1a-FIG. 1c show typical results for the HDL two-dimensional gel electrophoresis test. In the example shown in FIG. 1b, a patient with CVD has less of α-1 HDL and α-2 HDL, and more of preβ-1 HDL. High levels of α-1 and α-2 are associated with low risk for CVD, while high level of preβ-1 HDL is associated with high risk for CVD. The results of HDL subpopulation analysis will allow the healthcare practitioner to more effectively treat patients with agents, such as various statin drugs and niacin, to normalize these particles and decrease CVD risk.

Cholesterol production and absorption are important aspects of CVD risk, and thus should be assessed. People have elevated total cholesterol and LDL cholesterol for a variety of reasons. One reason is that they make too much cholesterol in their body, and such people are ideal candidates for statin treatment to inhibit cholesterol production. Other people have high cholesterol and LDL cholesterol because they absorb too much cholesterol in their intestines. Such people are ideal candidates for diet and cholesterol absorption inhibitors. Testing of plasma sterols is a means for assessing such risk, and comprises the testing of the following: lathosterol (a marker of cholesterol production); desmosterol (a marker of cholesterol synthesis); and beta sitosterol, campesterol and cholastanol (markers of cholesterol absorption). The results of such testing reveal whether a person is a hyper-absorber or a hypo-absorber, or is a high producer or normal producer of cholesterol.

The results from the plasma sterol testing for cholesterol absorption and production enable the healthcare practitioner to treat elevated LDL cholesterol more effectively. This will assure the use of the most appropriate treatment at the initiation of drug therapy: a more effective statin, a cholesterol absorption inhibitor, or a combination of both. It has been shown that the use of statins not only decreases cholesterol synthesis, but also increases markers of cholesterol absorption. This may explain why low dose statins are almost as effective as high dose statins in reducing LDL cholesterol. Doubling the dose of a statin, on average, only increases the LDL lowering effect by about 6%. This may also explain why adding a cholesterol absorption inhibitor to low doses of a statin is often much more effective in LDL cholesterol control than increasing the dosage of any statin to the maximum dosage. Addition of a cholesterol absorption inhibitor to any statin therapy usually reduces LDL cholesterol by an additional 15-18%.

The measurements of cholesterol absorption and production also enable the diagnosis of rare disorders of cholesterol metabolism associated with increased heart disease risk. The analysis can identify diseases, such as phytosterolemia and cerebrotendinous xanthomatosis, both of which are eminently treatable.

Genetic causes of heart disease also pose a great risk, and thus should be assessed. About 20% of the population carries the apoE4 genotype and these people have higher cholesterol absorption, higher LDL cholesterol levels, and higher heart disease risk than those who do not carry the apoE4 genotype. Apolipoprotein E genotyping is a means for assessing CVD risk by testing a person's DNA. Knowing the apoE genotype of a patient will enable the treating healthcare practitioner to optimize an individual's therapy as subjects carrying the apoE4 allele are more sensitive to dietary modification and less sensitive to statins in terms of LDL-C lowering.

ApoE is found on triglyceride-rich lipoproteins and HDL, and it is important for liver uptake of remnant lipoproteins. ApoE's major function is to serve as a ligand to LDL receptor for lipoproteins containing apoB and apoE or containing only apo E. The plasma concentration of apoE is about 10 mg/dL, and its molecular weight is 34,145 Daltons. There are three different apoE forms in human plasma, which are apoE2, apoE3 and apoE4. The various forms of apoE bind to the apoE-specific cell surface receptor with different affinity, leading to differences in clearance of the apoE containing VLDL and chylomicron remnants by the liver. ApoE3 is the common form with cysteine at residue 112 and arginine at residue 158. ApoE4 is a somewhat less common form, with arginines at both residues 112 and 158. Patients with apoE4 catabolize LDL at a slower rate than apoE3 patients. Apo E4 has been associated with increased risk of CVD and dementia. ApoE2 is the least common form; patients with apoE2 catabolize LDL faster than others, but those with the apoE2/2 genotype are at increased risk for developing dysbetalipoproteinemia or type III hyperlipoproteinemia.

Studies have shown that the presence of the genetic form apoE4, found in about 20% of the population, increases intestinal cholesterol absorption, liver uptake of cholesterol, LDL cholesterol, heart disease and dementia risk, and responsiveness to diet. The same form (ApoE4) decreases response to statins in terms of lowering LDL cholesterol. Knowledge of the patient's apoE genotype, along with the other markers, enables the healthcare practitioner to provide more effective treatment of an individual in terms of controlling LDL cholesterol and reducing the heart disease risk with diet and medications.

The testing of a patient with the extended panel disclosed herein may be carried out in any suitable facility, including, but not limited to, a hospital, a healthcare clinic or facility, a healthcare practitioner's practice facility, or a laboratory or medical testing or imaging facility. The testing may be carried out at a variety of suitable facilities, depending on the test, and the test results from each facility are delivered or transmitted for evaluation or analysis that will be performed utilizing the test results from all of the facilities for a given extended panel testing. The testing may be conducted by a healthcare practitioner, a nurse, or a lab technician. The results of the testing may be stored at one or more local storage facility, one or more remote storage facility, or any combination thereof. The results of the testing may be accessed from one or more such storage facilities for the performance of the diagnosis or diagnosis and treatment analysis. Preferably, the results are stored in digital format. The digital test data may be submitted for analysis, preferably via a communication between each storage facility and the processing device in communication with the application embodying the CVD diagnosis and treatment protocol algorithm.

In one embodiment of the present invention, cardiovascular risk is assessed, via the use of the extended risk panel of the present invention, by testing the general metabolic factors, specialized heart disease factors, specialized lipid factors, and new important factors associated with CVD risk, such as HDL particles by two-dimensional gel electrophoresis, sdLDL-C, cholesterol synthesis and absorption markers, inflammatory markers, glucose homeostasis markers, and NT-proBNP.

In one embodiment of the present invention, the risk of recurrent CVD events in individuals who have already experienced one or more CVD events is assessed. These patients usually have very low level of α-1 HDL particle levels. The risk for recurrent or new CVD event is increased when the concentration of α-2 HDL is also significantly lower than normal.

In one embodiment of the present invention, the efficacy of drug therapy, such as lipid-altering medications, is evaluated. The result of the efficacy evaluation is utilized in the planning of a more personalized treatment. The effect(s) of a given drug on CVD risk reduction is monitored based on established information, particularly the established information that the HDL subpopulation profile is a significant and sensitive CVD-risk marker and superior to HDL-C in risk assessment and that the different lipid lowering medications have various effects on the HDL subpopulation profile. In one embodiment of the present invention, the effect of a given drug on the LDL-C, sdLDL-C, HDL-C, TG, LpPLA2, and CRP levels, as well as on the HDL subpopulation profile, and cholesterol synthesis and cholesterol absorption markers, is monitored.

2.2 the CVD Diagnosis and Treatment Protocol Algorithm

Figure 3A:
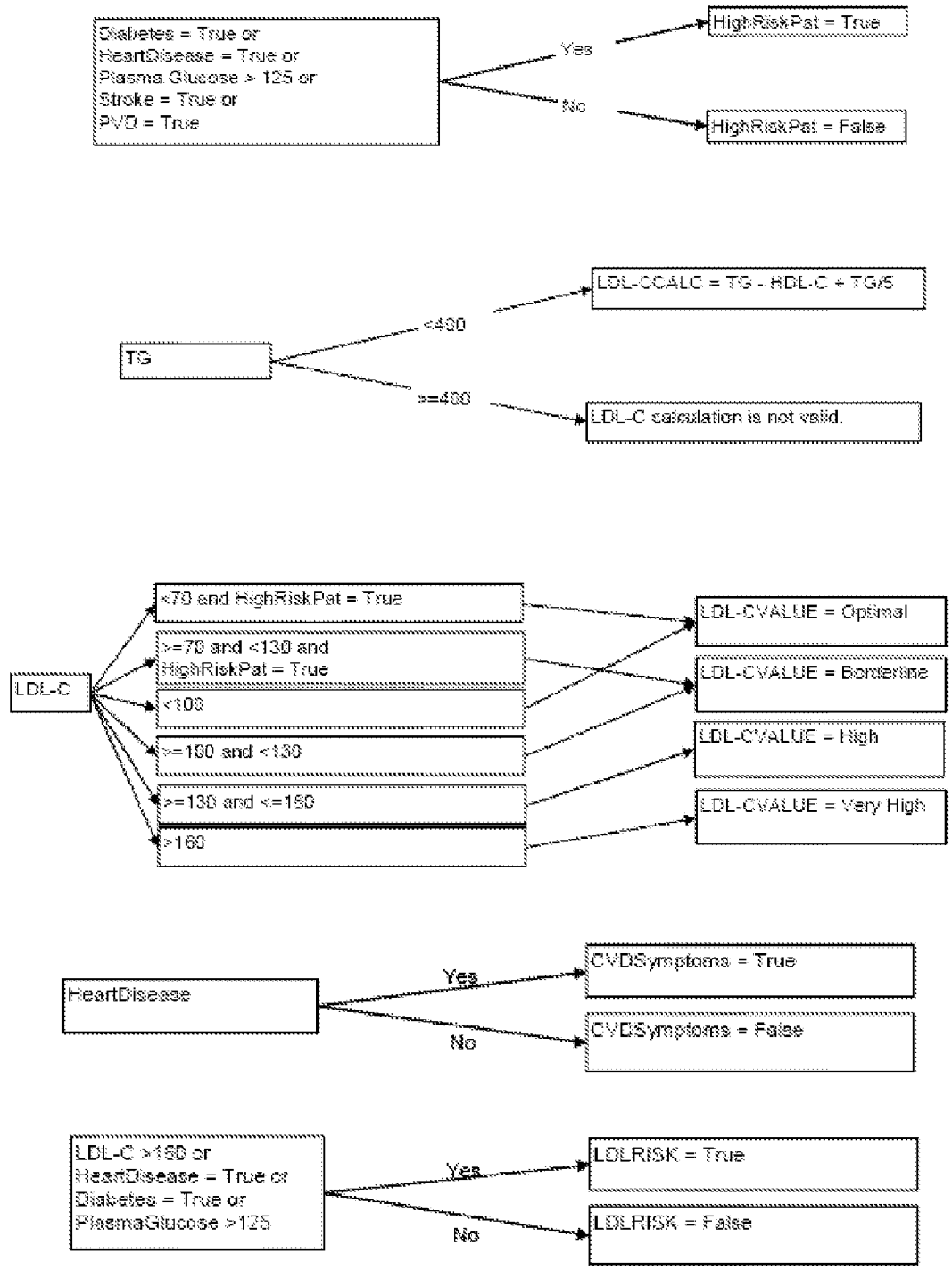
FIGS. 3A-3R provide a flowchart depicting the various aspects of the CVD diagnosis and treatment protocol algorithm for performing diagnosis analysis or diagnosis and treatment analysis, according to one embodiment of the present invention.
Figure 3B:
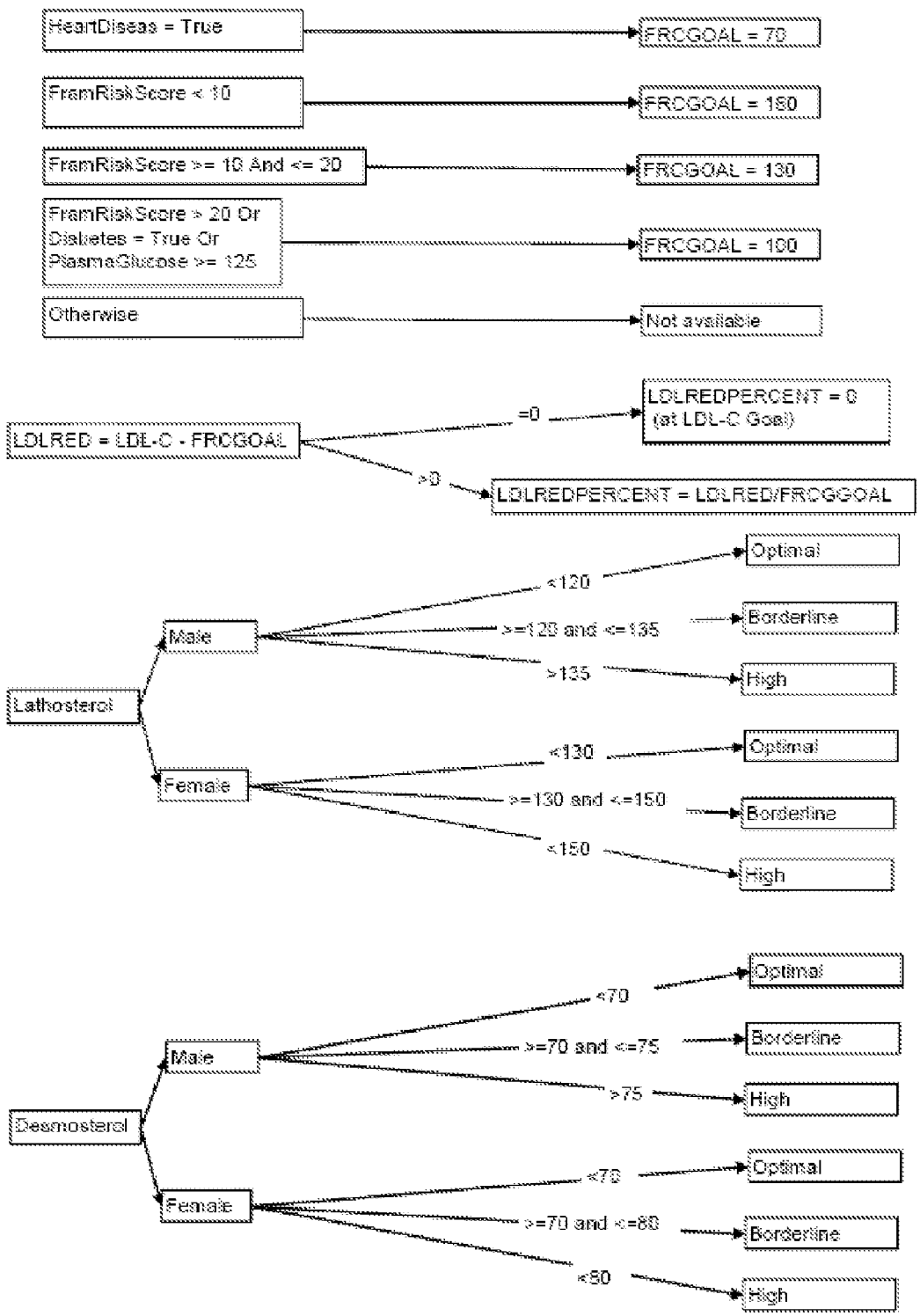
Figure 3C:
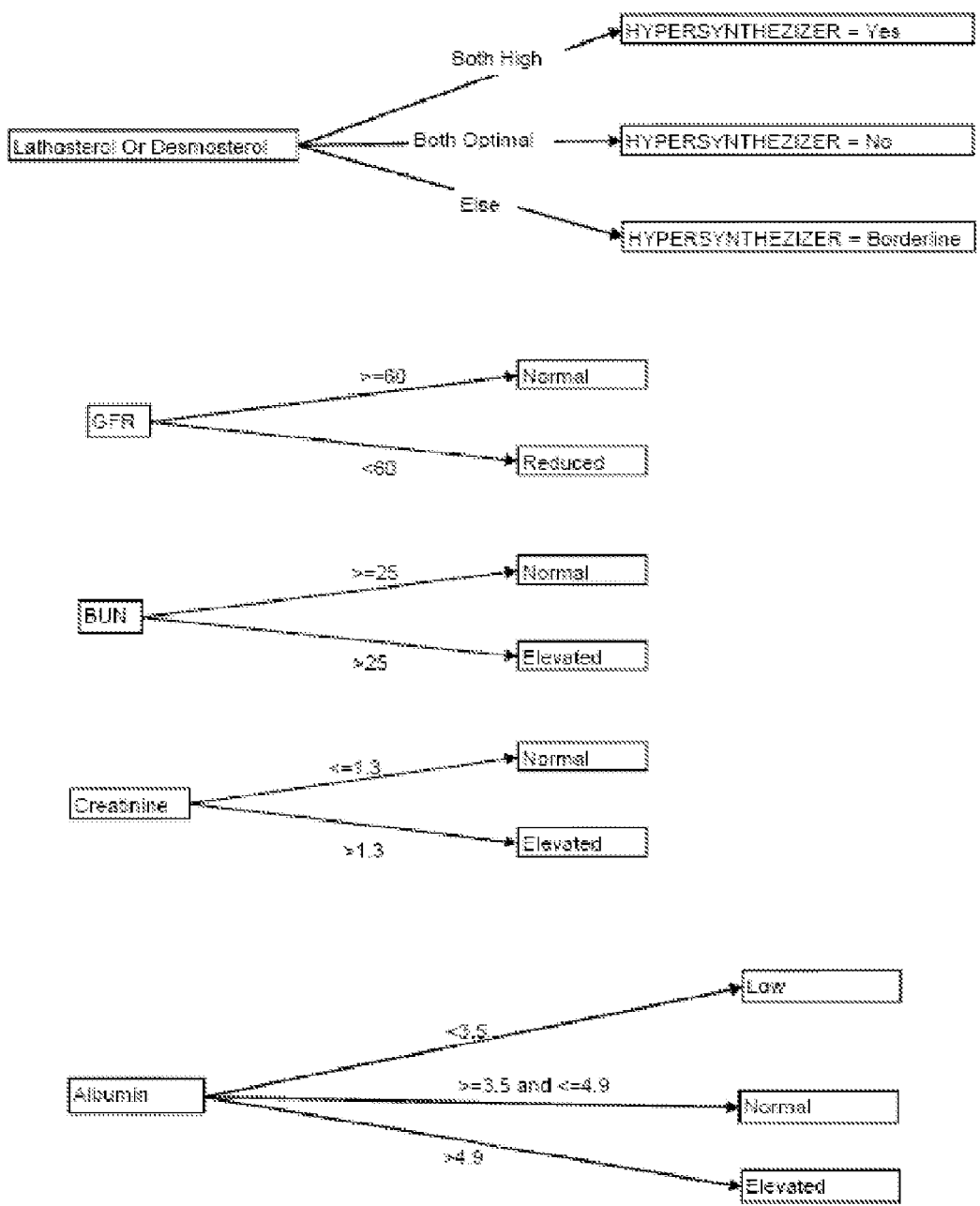
Figure 3D:
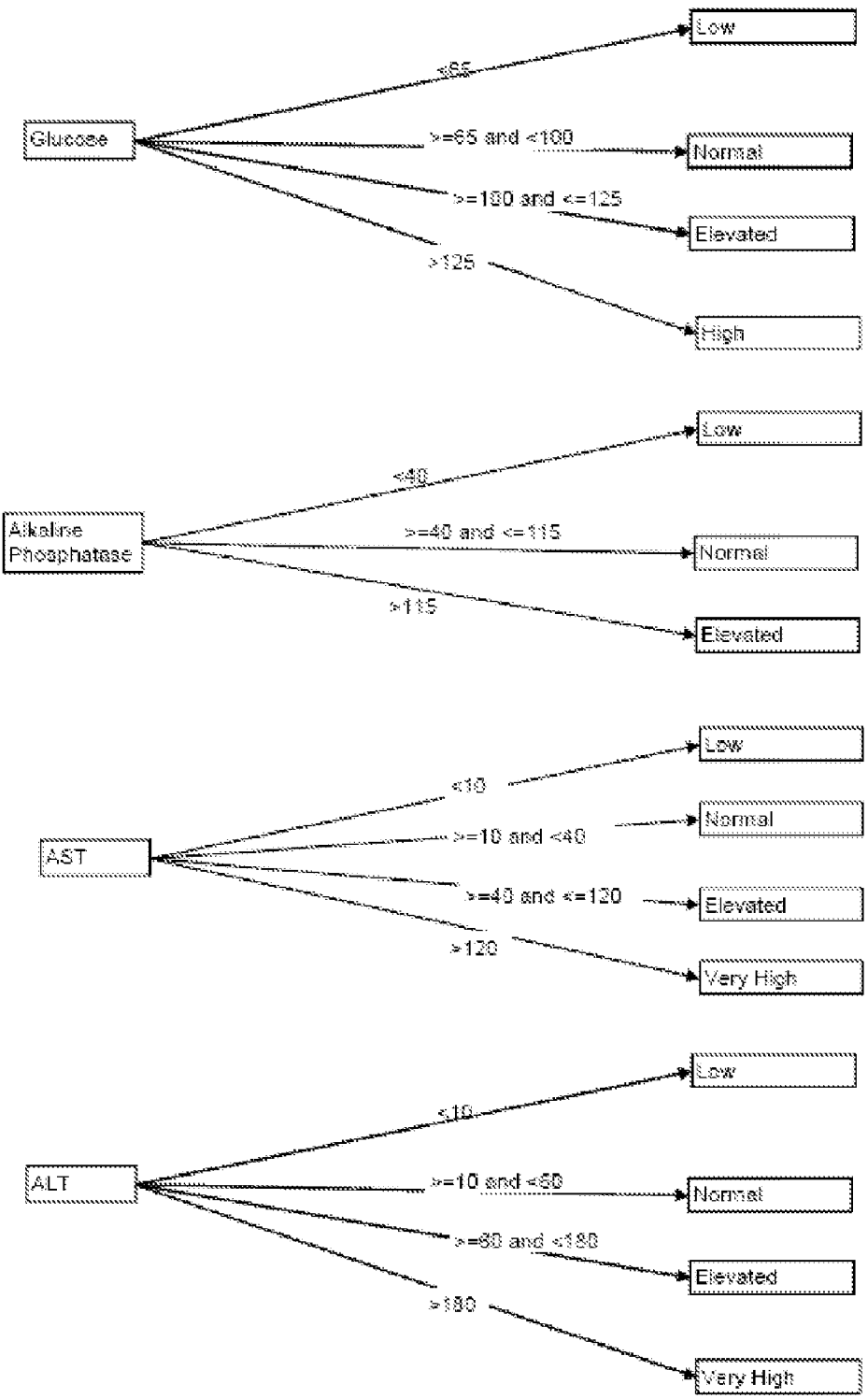
Figure 3E:
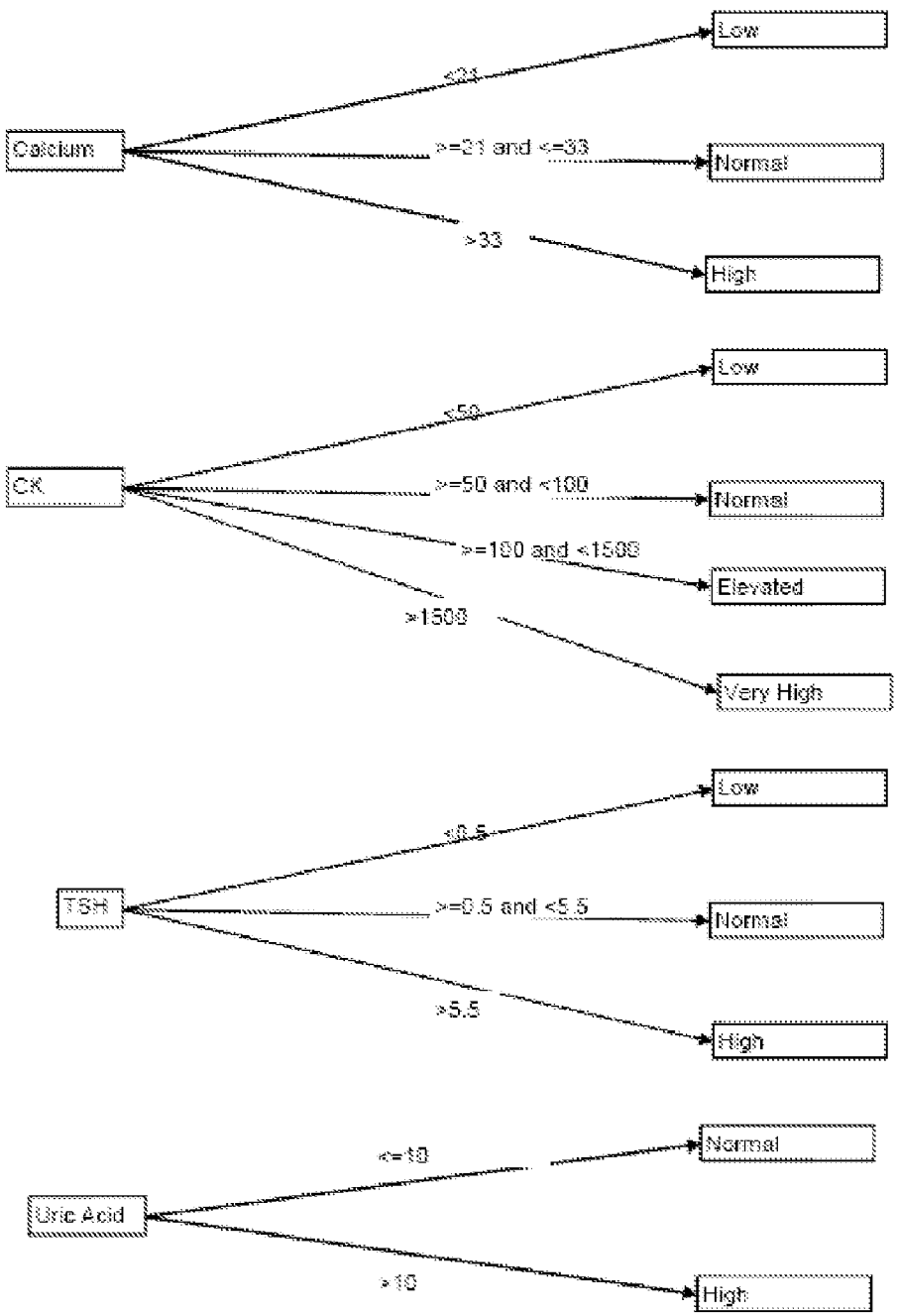
Figure 3F:
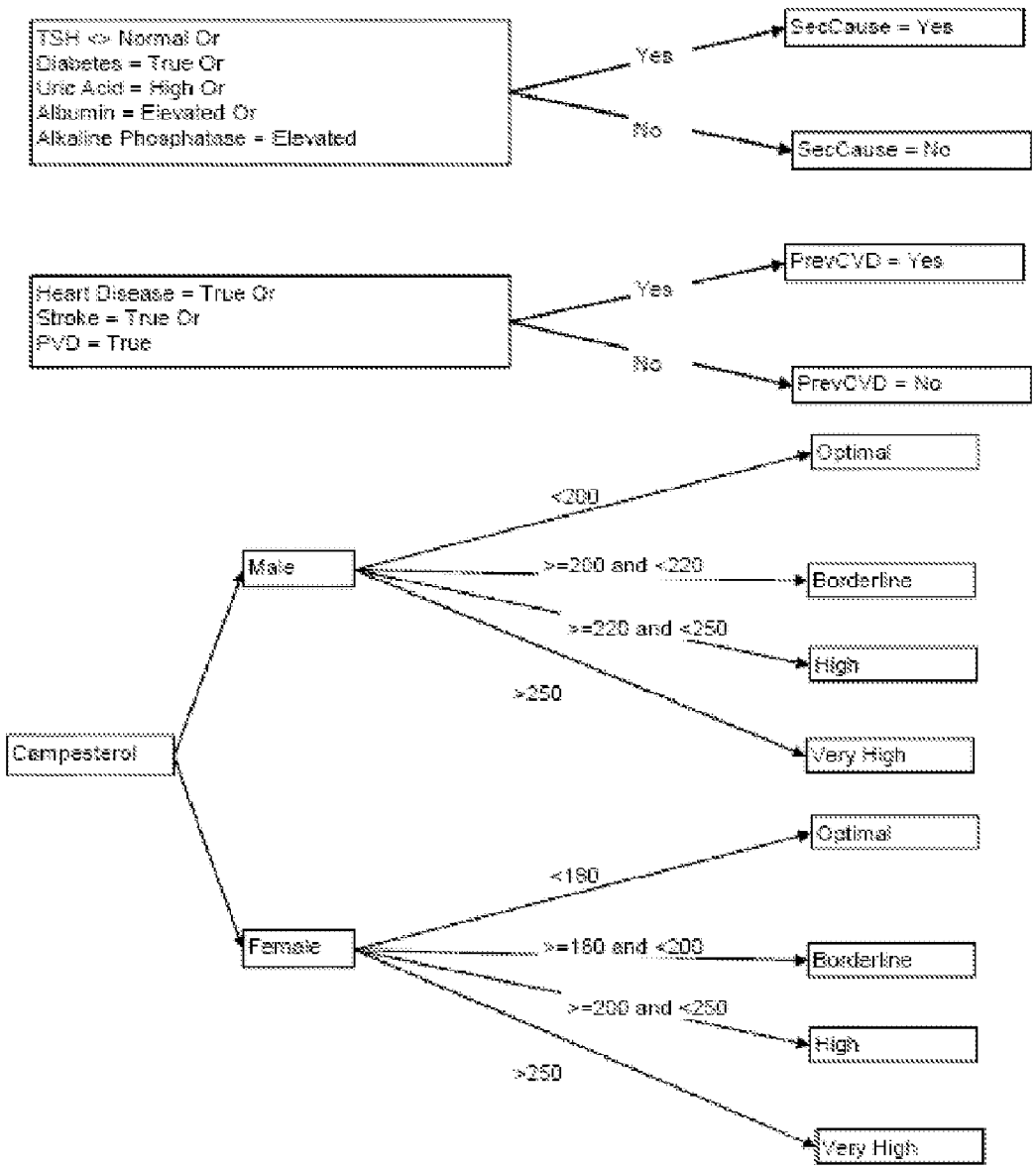
Figure 3G:
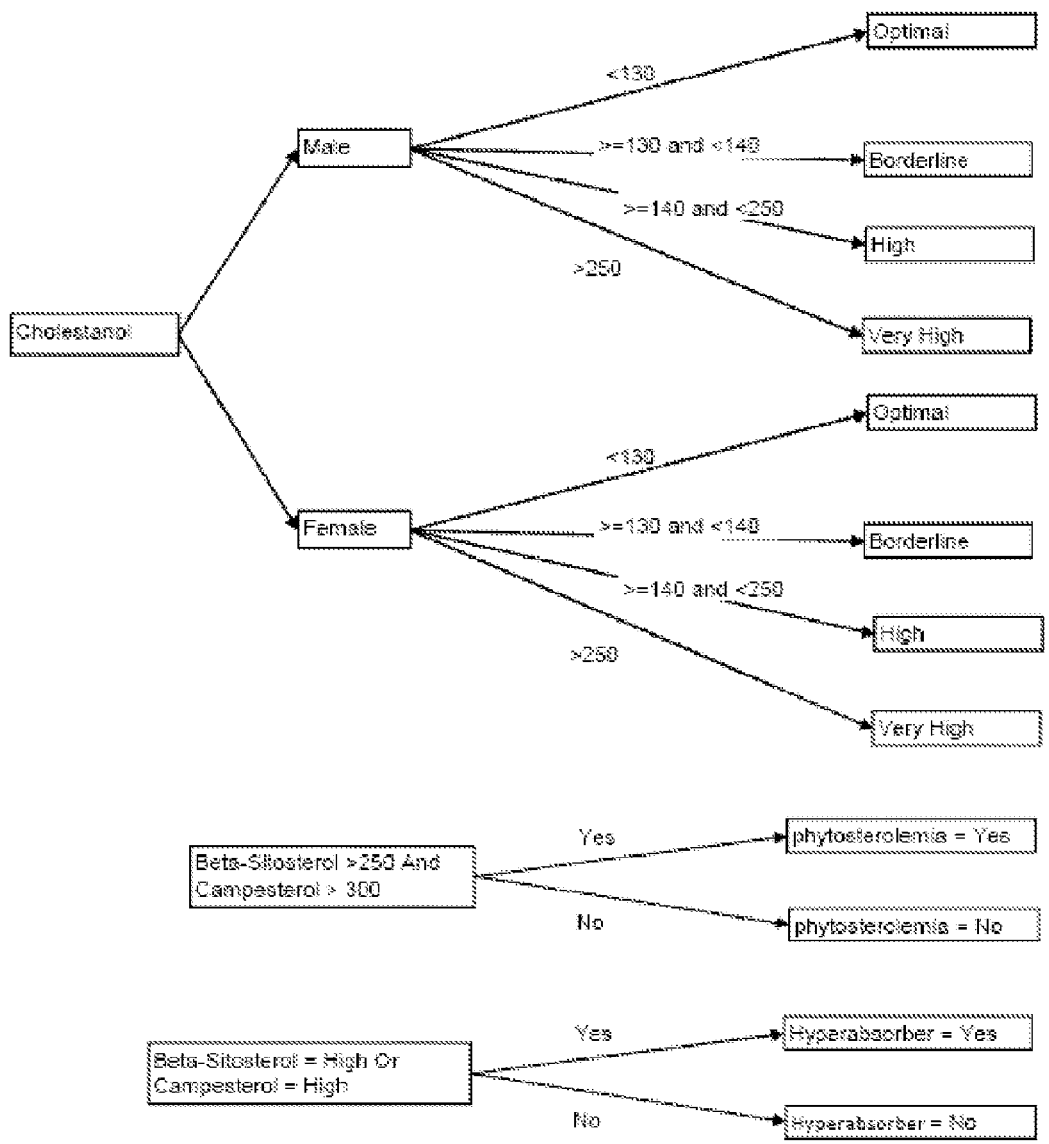
Figure 3H:
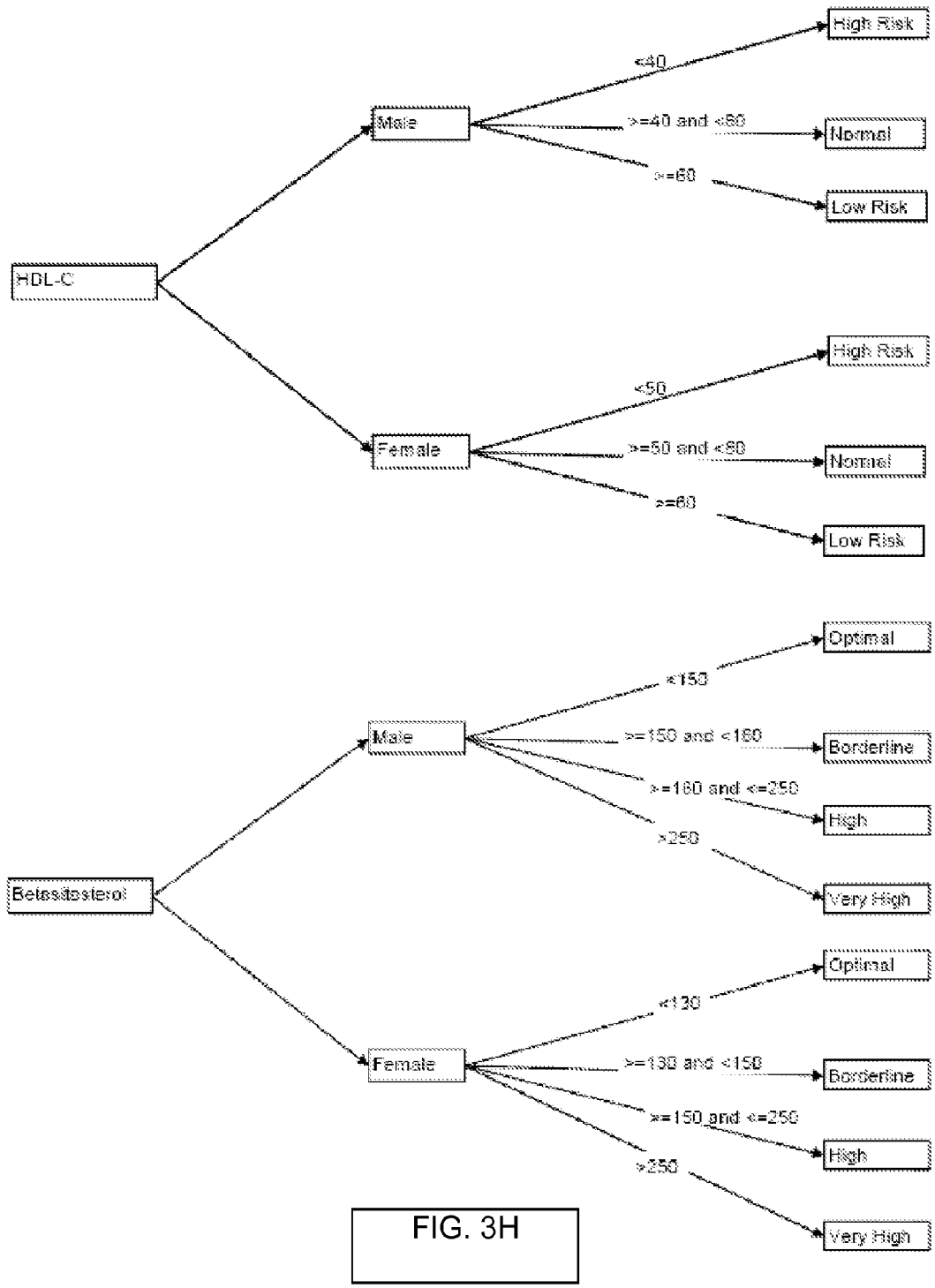
Figure 3I:
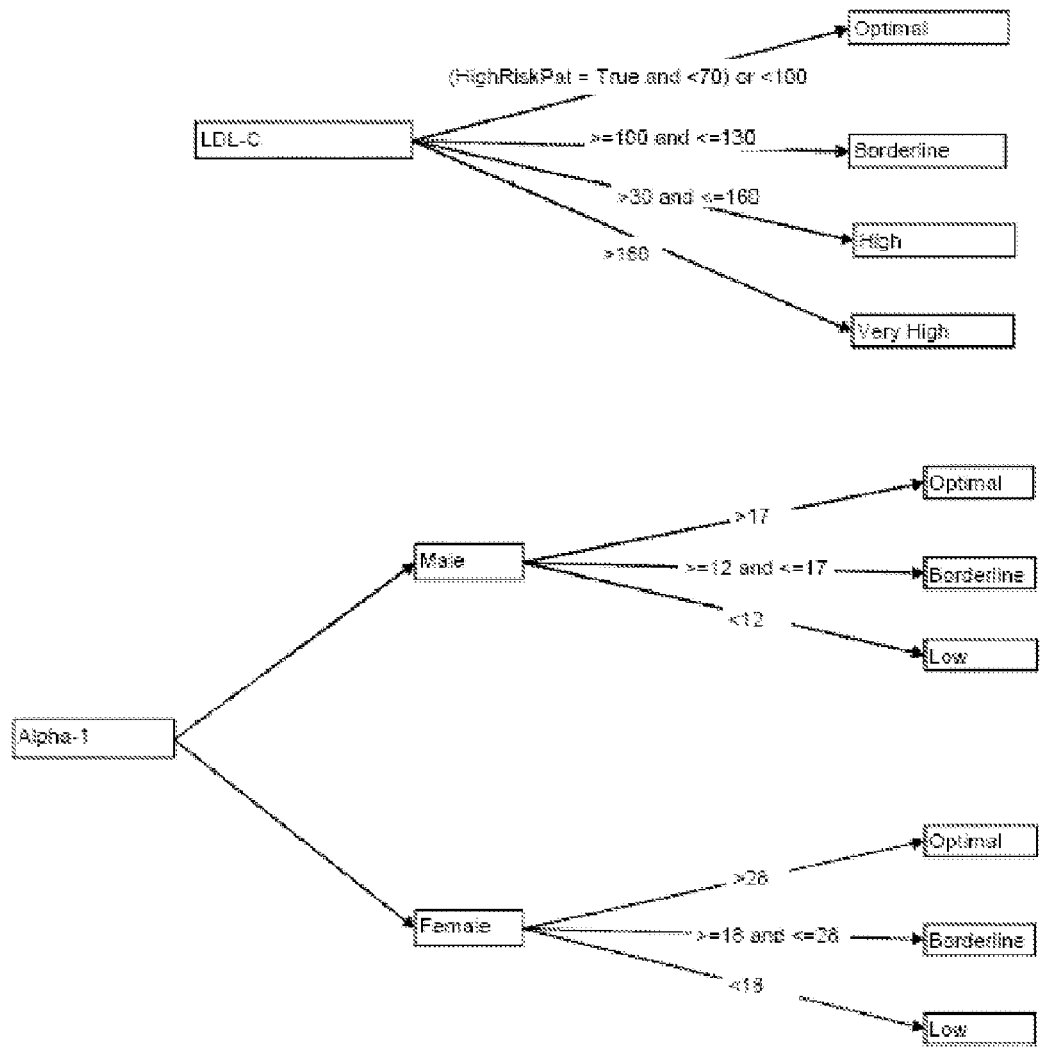
Figure 3J:
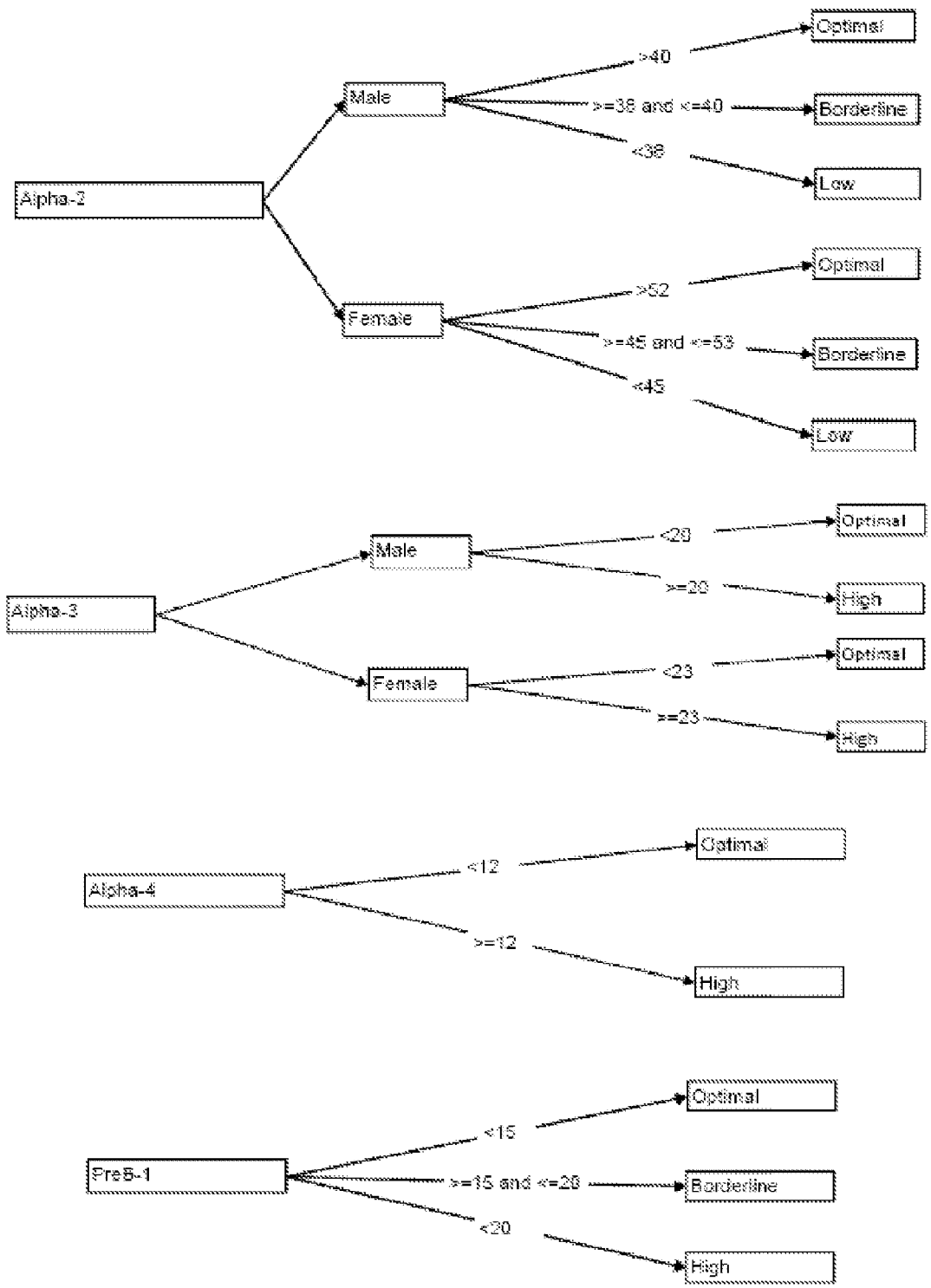
Figure 3K:
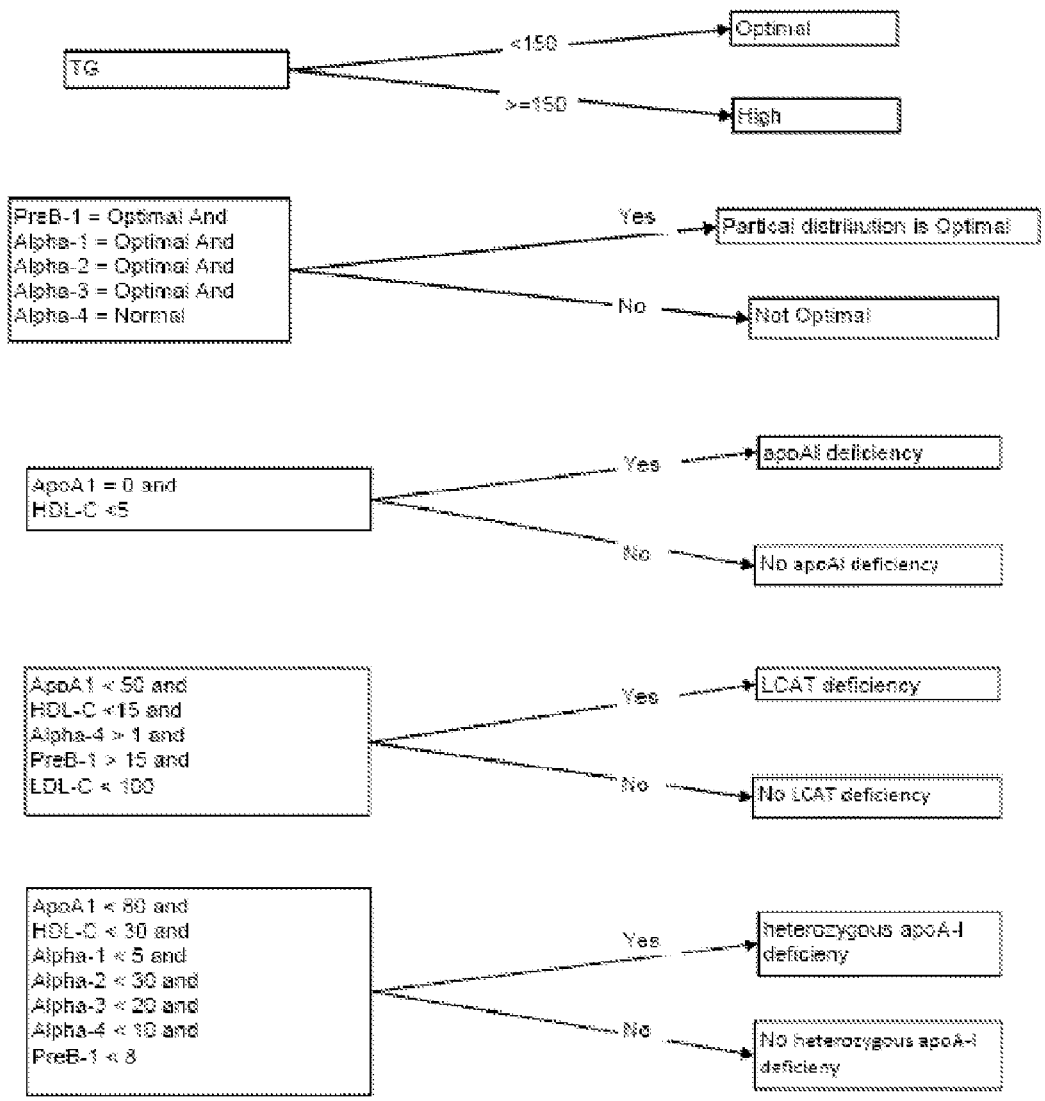
Figure 3L:
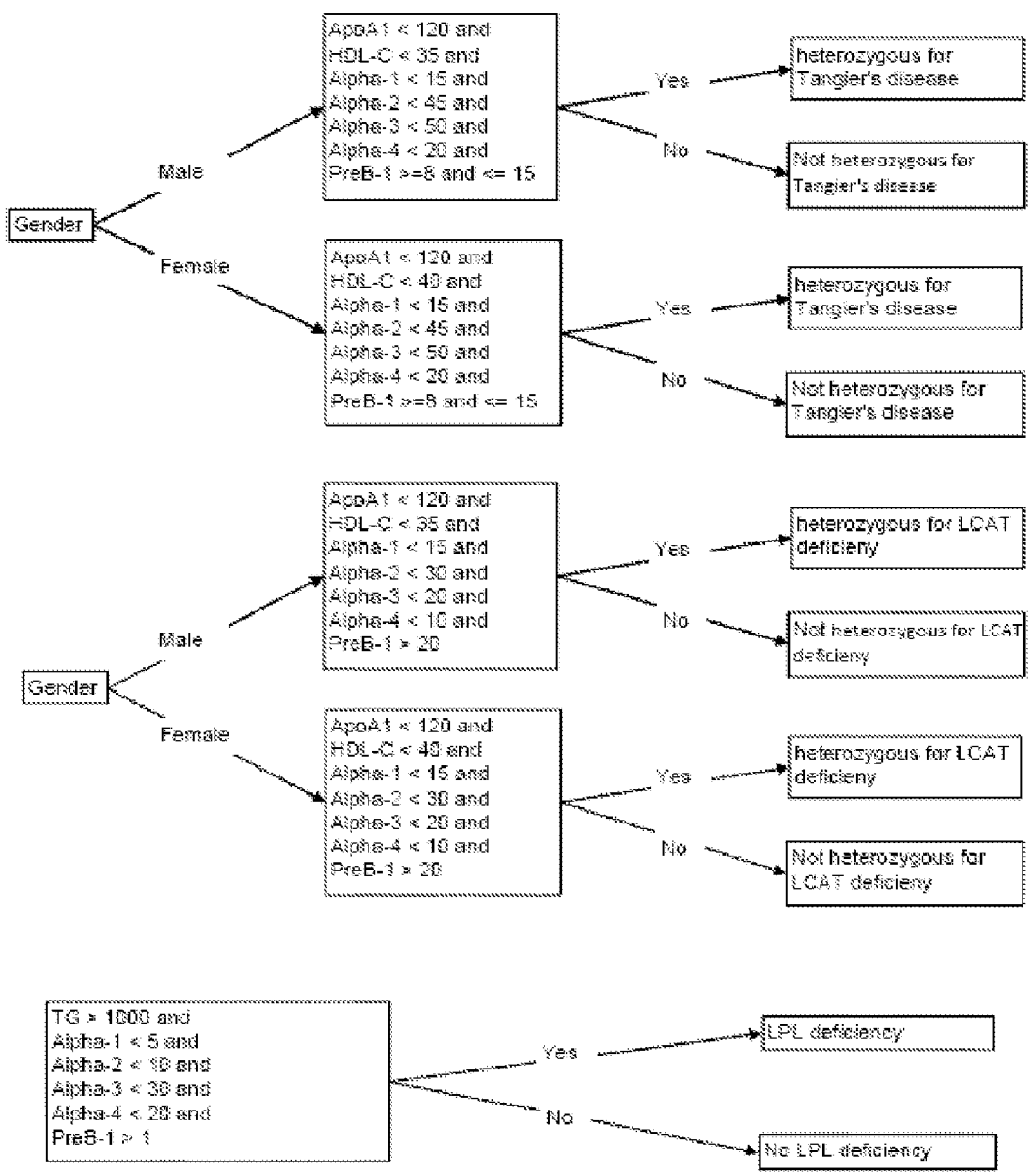
Figure 3M:
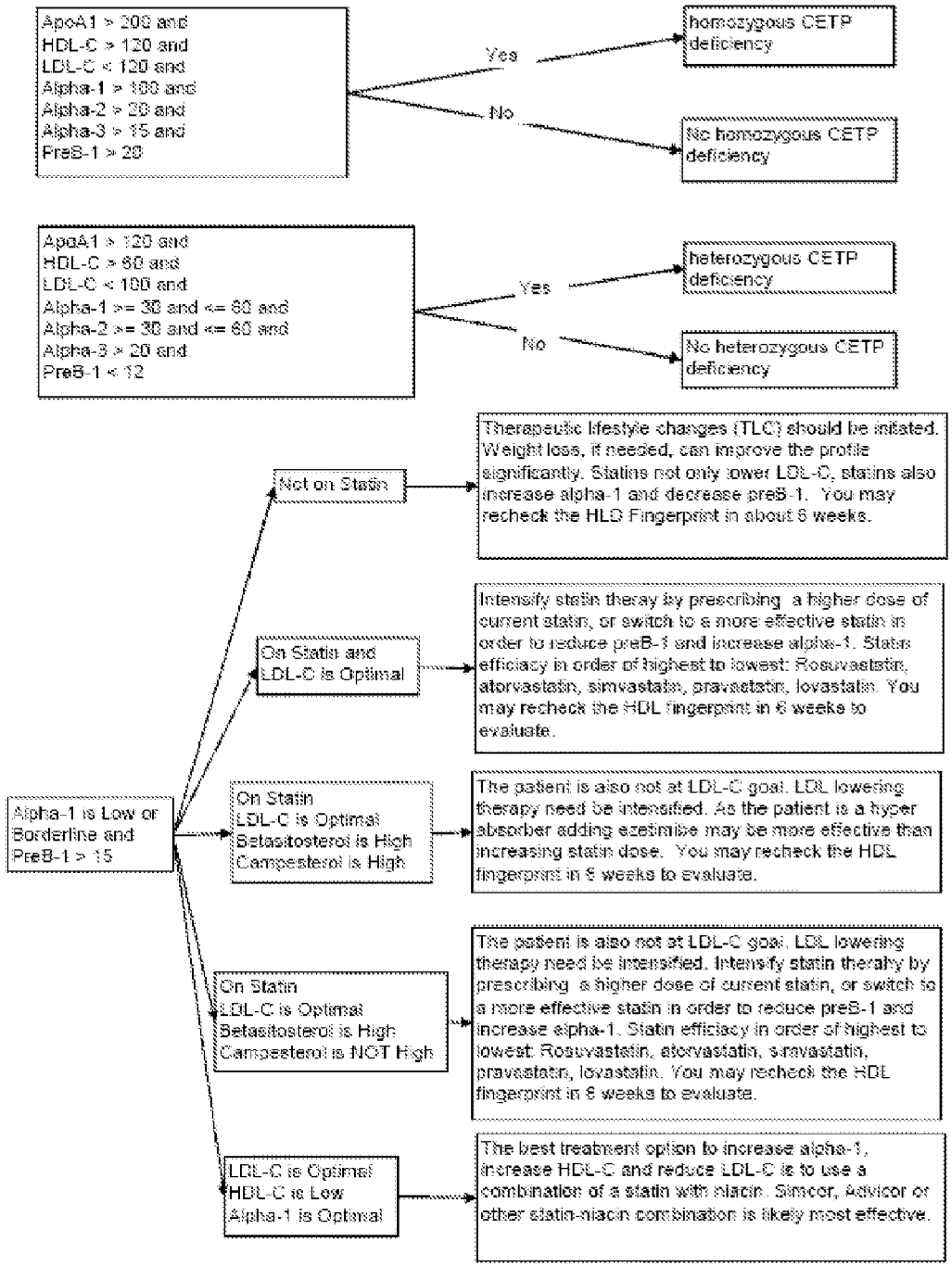
Figure 3N:
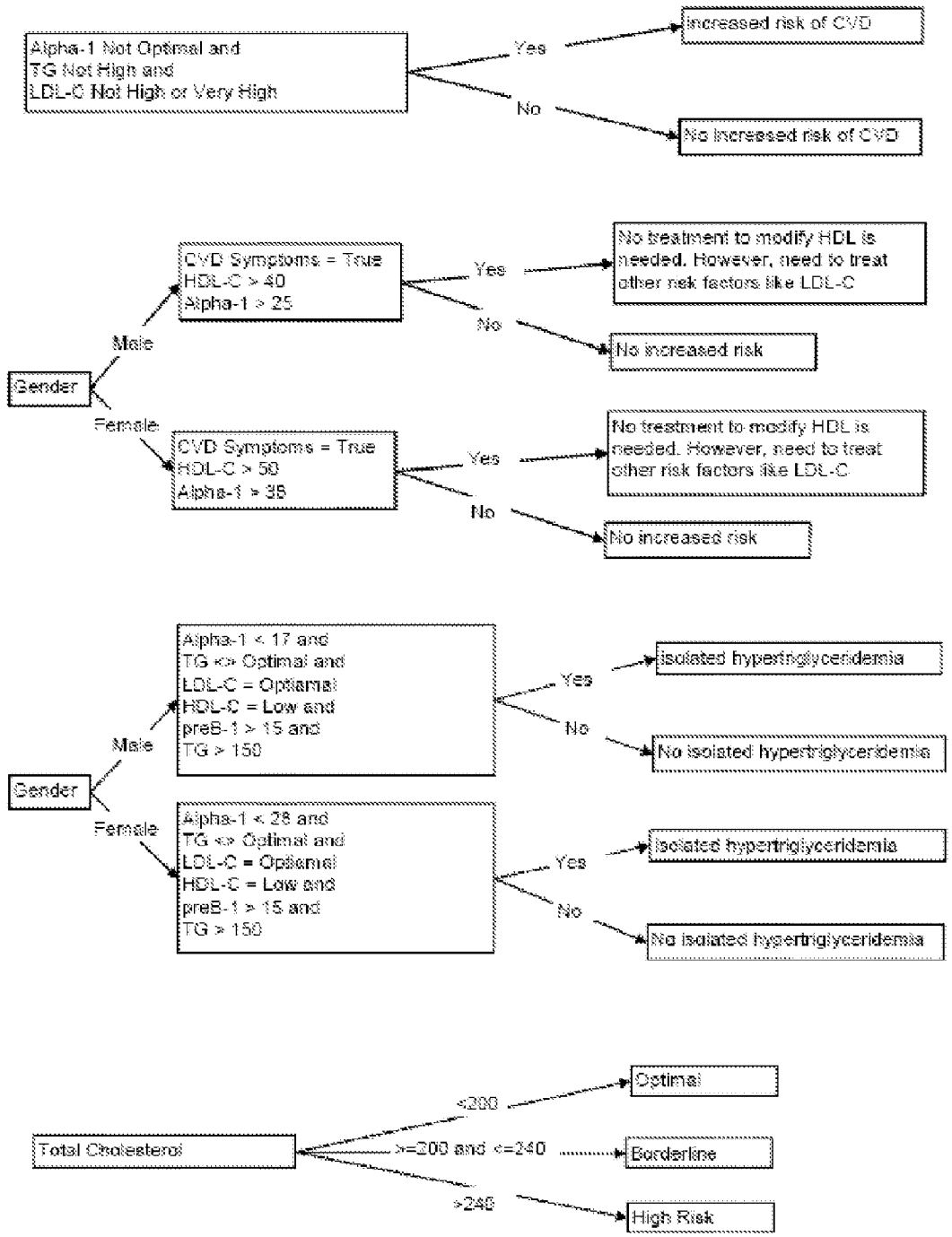
Figure 3O:
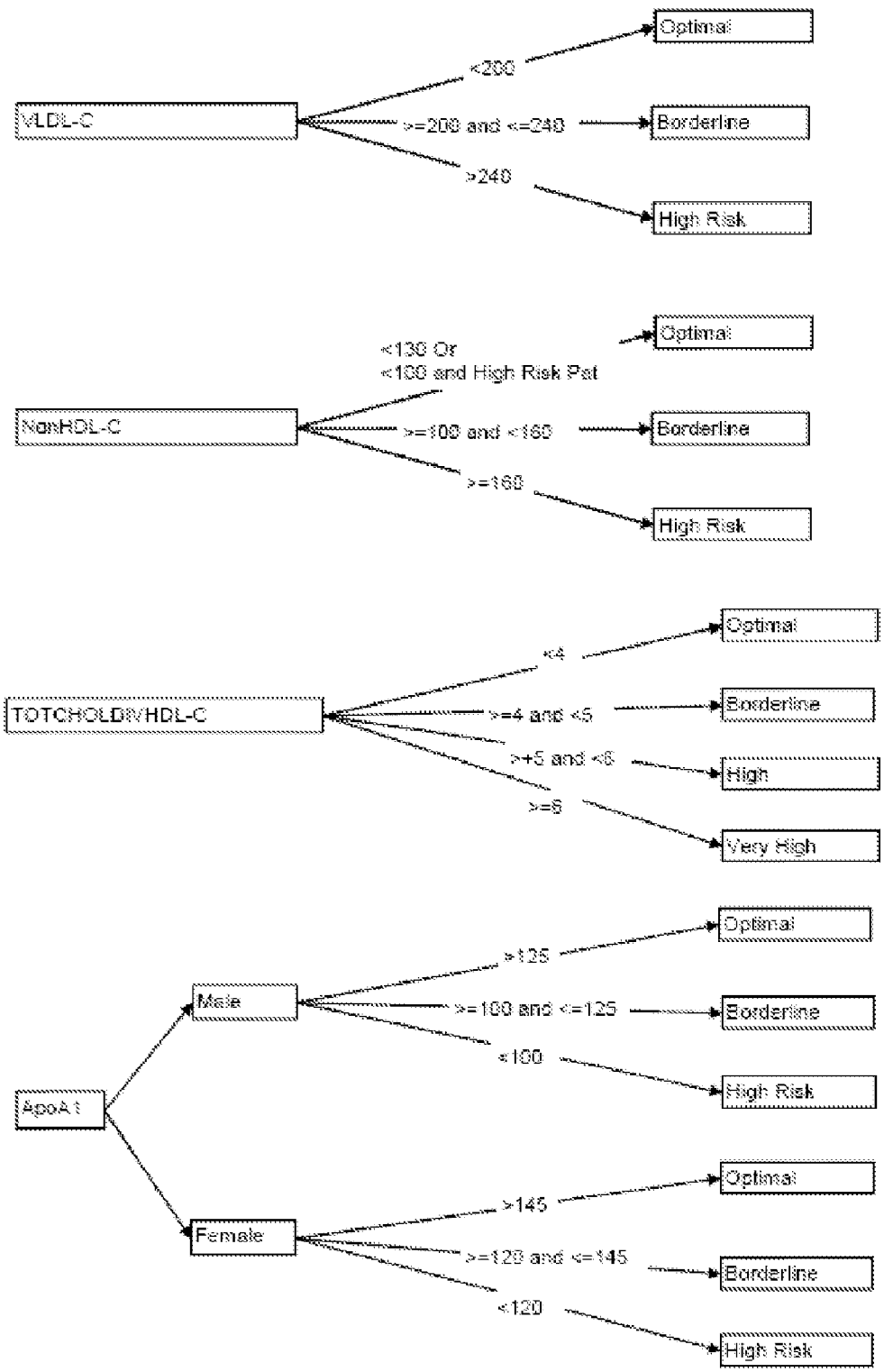
Figure 3P:
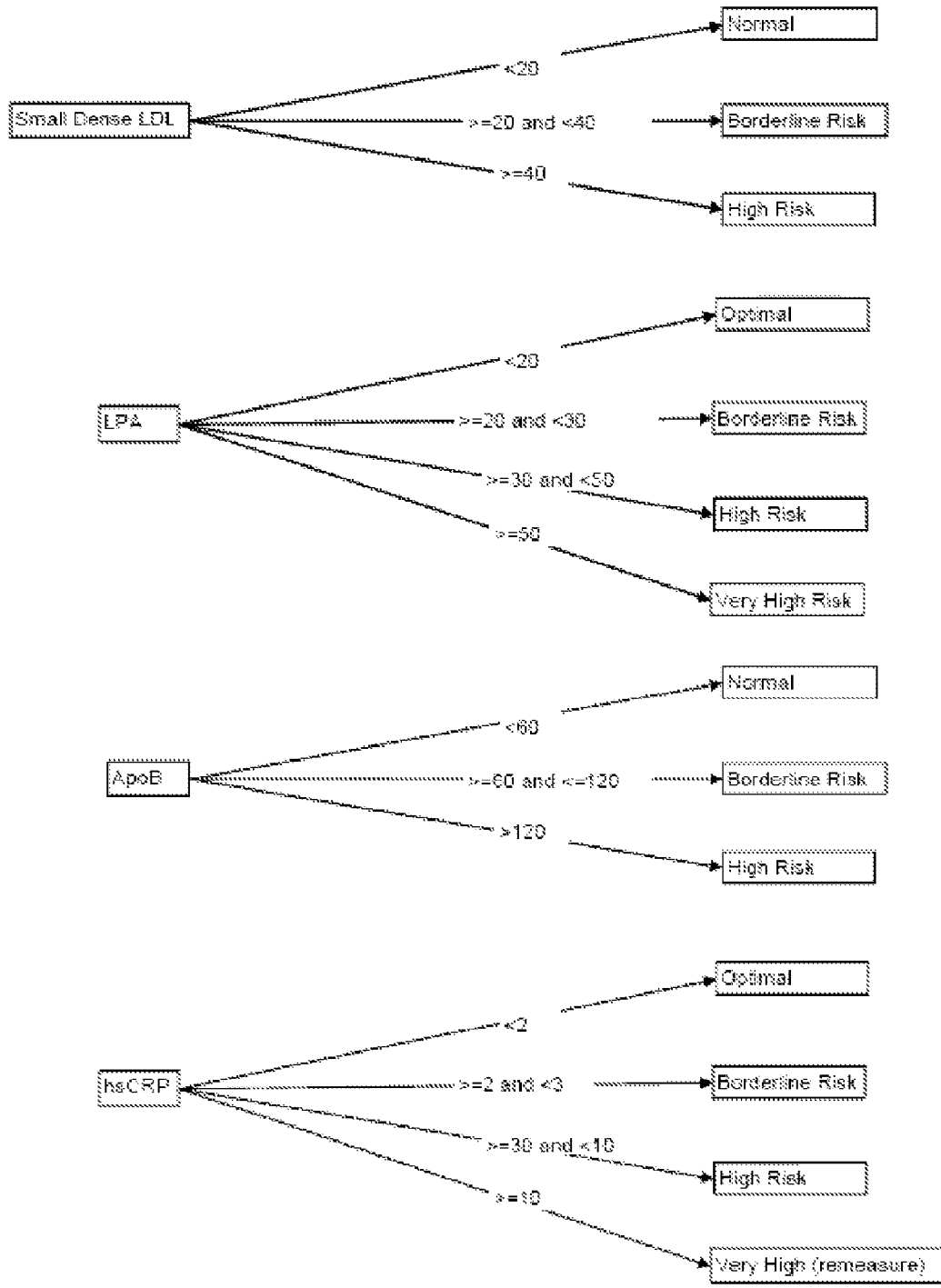
Figure 3Q:
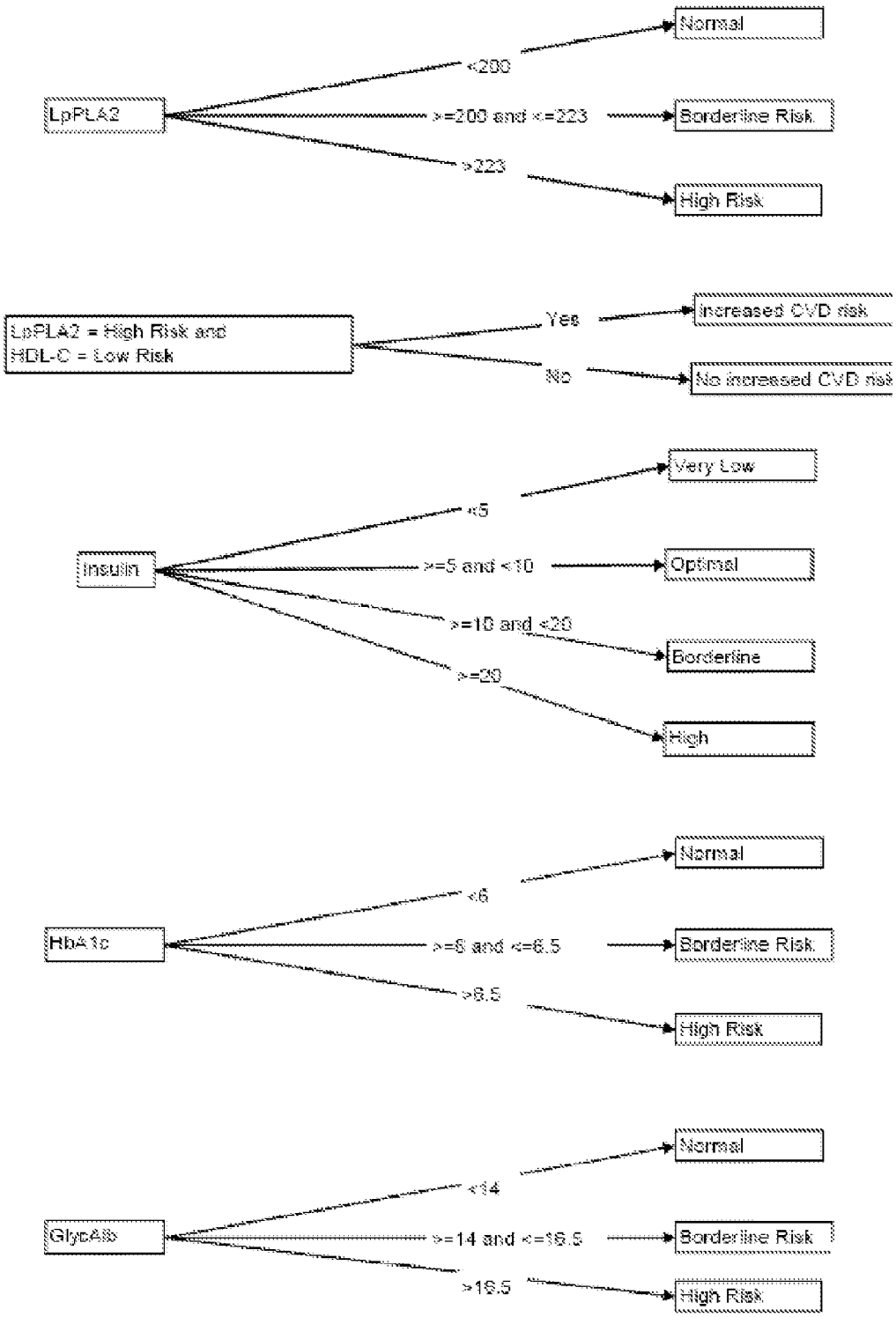
Figure 3R:
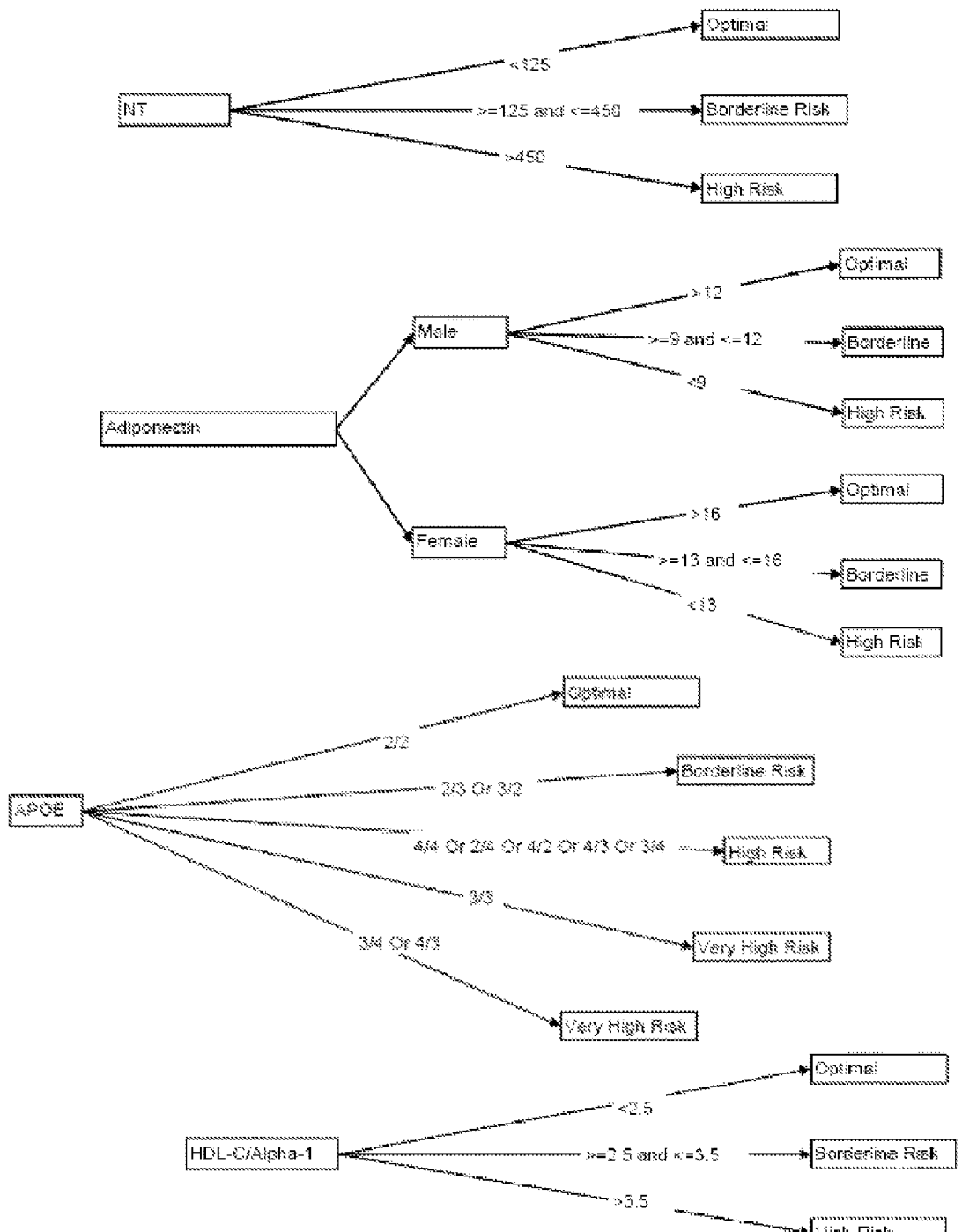

A patient's diagnosis and treatment plan for a cardiovascular disease related disorder or risk are determined via the analyses performed in accordance to the CVD diagnosis and treatment protocol algorithm of the present invention, aspects of which are illustrated in the flowchart depicted in FIGS. 3A-3R. The present algorithm has been developed to assist the healthcare practitioner, as well the patient, in the management of the patient's healthcare. The algorithm addresses all relevant factors necessary to make a comprehensive evaluation, and facilitates an accurate diagnosis based on statistical data accumulated from broad range of studies. The general method for personalized diagnosis and treatment of a patient utilizing this algorithm is depicted in FIG. 4. Utilization of such an algorithm to perform an analysis for diagnosis or diagnosis and treatment of a CVD or risk therefor not only provides a more accurate diagnosis and personalized treatment plan, but also makes the process quicker than the traditional analysis. The savings of time would not only lead to earlier treatment of a patient, but also would provide potential cost savings (e.g., to the patient, the insurance companies, the medical facilities, and/or the healthcare practitioner). Further, use of such an algorithm could lead to standardizing the practice, and hence reduce likelihood of misdiagnosis.

The flowchart of FIG. 3A-3R is a simplified representation of the paths or the stepwise iterations of the diagnosis analysis performed to yield a personalized diagnosis or a personalized diagnosis and treatment plan for a patient. For the formulation of the diagnosis, the analysis comprises a series of iterative steps, each successive step evaluates each new data (i.e., result of a test from the extended risk panel) in combination with all data previously submitted in the previous steps in the cycle and relevant information about the patient initially submitted, (said evaluation being performed in comparison to statistical data included as part of the algorithm to enable this process), until all test data entered or submitted for analysis are evaluated comprehensively. Upon the completion of the final step, the analysis function terminates, and the diagnosis result is formed upon the completion of the analysis function. The present invention also contemplates the modification or update of statistical data, which is included as part of the algorithm, with current statistical data as such data becomes available and would serve to improve the accuracy of the diagnosis and treatment results. For the formulation of the treatment plan, the analysis comprises a series of successive iterative steps, as in the diagnosis analysis, but continues the iterative steps to evaluate the diagnosis data in combination with other data entered in previous steps and the relevant data about the patient initially submitted, and in view of the statistical data.

The diagnosis and treatment protocol algorithm of the present invention may be embodied in any suitable application, such as a computer program or code, that can facilitate its use; said algorithm or the application embodying said algorithm may be stored in a hard-drive of a computer (internal or external), a portable drive or disc, a server, a temporary or permanent memory device, or any other storage means that can facilitate the use of the algorithm and/or the results derived from the use thereof. The algorithm (or the application embodying it) may be distributed, gratis or for compensation, to other healthcare practitioners or healthcare facilities, preferably to expand its use for the benefit of greater number of patients. The algorithm or the application is preferably in communication with at least one processing device that facilitates the diagnosis analysis or diagnosis and treatment analysis, and which may be, for example, a computer or network processor. The algorithm or the application that embodies it may be accessed locally (e.g., on a single or networked computer) or remotely (e.g., web-based network via the internet, or via an intranet). This access to the algorithm or the application may be facilitated via the use of any suitable equipment, including, but not limited to, a computer, an internet appliance, telephonic device, a wireless device, and the like. Access to or the use of the algorithm or the application embodying said algorithm or the results obtained from the use of the algorithm may be limited or secured from general access or use, e.g., via a password, encryption, biometric or voice-activation, or any suitable protection or security means. The algorithm of the present invention may be accessed by any authorized party, e.g., a healthcare professional or lab technician. A patient's personal information, which includes but not limited to, name, address, age, contact information, and previous medical history, and/or clinical data, for example, results of the extended panel testing and relevant information about the patient, may be entered or submitted, locally or remotely for processing, said processing includes the performance of the diagnosis analysis or diagnosis and treatment analysis. The results from said processing may be obtained by, or delivered or transmitted to, an authorized party, e.g., a healthcare professional, a healthcare facility or employees thereof, the patient or one who is acting on behalf of the patient, or patient's health insurance company; said obtaining or delivery or transmission may be performed locally or remotely; and, said results may be in digital, print or any other suitable format, and may be protected or secured via any suitable means. The delivery or transmission of the results may be automated, for example, with respect to delivery or transmission time and to the authorized parties for receipt thereof. The results may be delivered or transmitted via any suitable means, including, but not limited to, the Internet, an intranet, an electronic health record or management interface, telephone (land line, wireless, or VOIP), e-mail, facsimile, postal mail or in person. A patient's confidential information, such as the results of the extended testing and/or their analysis, any of the private information of a patient, results of other testing, and/or healthcare practitioner's notes and prescriptions, may be coded for delivery or transmission in order to preserve the confidentiality of such information. Said coding of patient information may be carried out in addition to any security or protection measures utilized for delivery or transmission of such information.

3. Method for the Individualized Treatment of Cardiovascular Diseases

The method of the present invention pertains to devising an individualized treatment plan based on the results of the diagnostic analysis performed utilizing the data obtained from the extended risk assessment panel testing. Such a treatment plan will ensure a more accurate and efficacious treatment of each individual. The "comprehensive" nature of the extended test panel also means that results from the extended panel testing are utilized in combination to diagnose a patient and devise a personalized treatment plan for that patient. The synergistic effect achieved from the use of the combined test results is far more superior, particularly with respect to accuracy, to diagnosis made based on results from only a limited set of tests, such as the tests for traditional risk factors.

The individualized treatment plan may address treatment of an existent cardiovascular disease, reduction of the risk of developing a cardiovascular disease, or a combination, in order to best manage the health care of an individual. The individualized treatment plan may comprise one component, for example, dietary restriction, or increased exercise activity, or single-agent drug therapy, or comprise multiple components, for example, dual-agent (combination) drug therapy or fish oil and single-agent drug therapy.

The methods of the present invention involve the use of an extended CVD risk assessment panel of the present invention to test a patient. Then, the results of said tests, in combination with relevant information about the patient, which include, but not limited to, gender, status as a smoker, diabetic, and obese, and liver, renal, and thyroid disfunctions, are utilized with the CVD risk diagnosis and treatment protocol algorithm of the present invention. The relevant information that is available for use herein may differ from patient to patient as to type/content of information and the extent of detail. In one embodiment of the present invention, the test results are entered into an application embodying said algorithm to facilitate processing and analysis thereof, to determine the cause of the patient's disorder or risk for CVD, which may be, for example, a lipid disorder, inflammatory stress, homozygous and heterozygous apolipoprotein A-I deficiency, ABCA1 deficiency, LCAT deficiency, CETP deficiency, phytosterolemia or cerebrotendinous xanthomatosis.

Figure 4A:
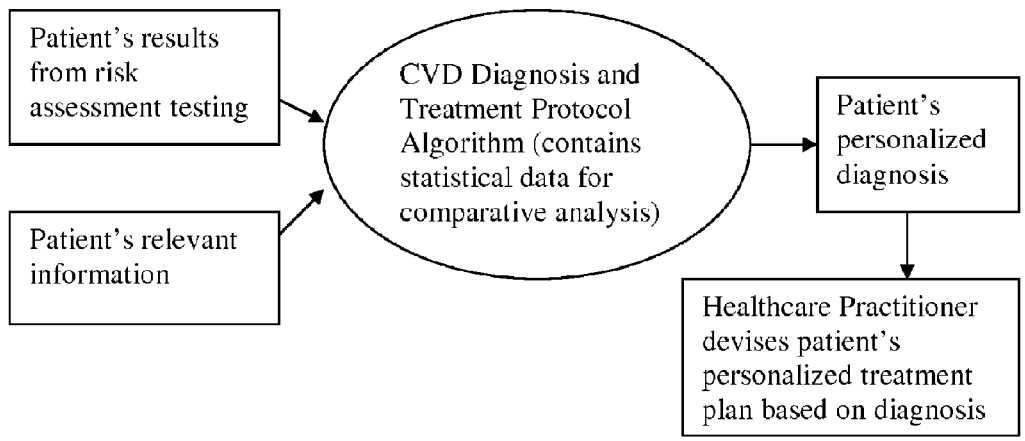
FIGS. 4A and 4B depict methods for performing a diagnosis and treatment analysis, according to certain embodiments.
Figure 4B:
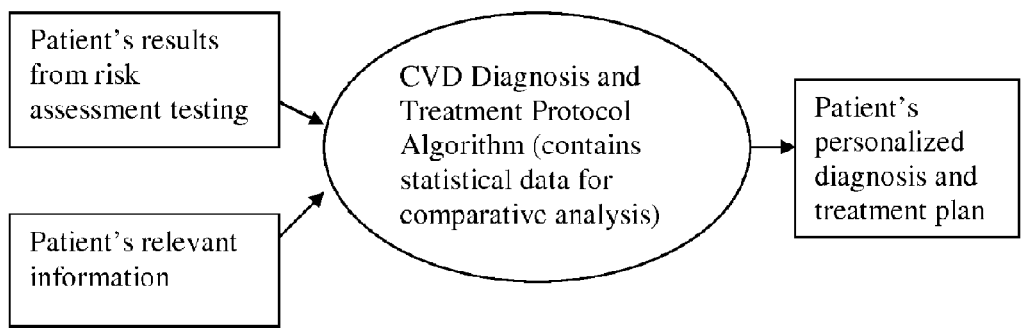

In one embodiment of the present invention, a healthcare practitioner utilizes the CVD risk protocol algorithm to perform diagnosis analysis utilizing the results of the complete extended CVD testing, said diagnosis analysis being performed comprehensively (i.e., the diagnosis is made based on all results from the complete extended risk panel and relevant patient information), interprets said results of the analysis, and devises a treatment plan personalized to the patient based on said interpretation of diagnosis analysis. In one embodiment, the diagnosis analysis is performed as an initial assessment of a patient, wherein the complete risk assessment panel is carried out for the patient. In another embodiment, the diagnosis analysis is performed as a subsequent assessment of a patient, wherein all tests except for genetic testing of the extended risk panel are carried out at a time period subsequent to the initial assessment testing; however, the diagnosis analysis is performed utilizing the results of this subsequent testing and the results of the initial genetic testing. In another embodiment, the diagnosis analysis is performed as a subsequent assessment of a patient, wherein all tests except for genetic testing and testing for plasma sterols of the extended risk panel are carried out at a time period subsequent to the initial assessment testing; however, the diagnosis analysis is performed utilizing the results of the this subsequent testing and the results of the initial genetic testing and testing for plasma sterols. In one embodiment of the present invention, the healthcare practitioner utilizes the results of the diagnosis analysis, in combination with relevant patient information, to devise a personalized treatment plan for the patient, as illustrated in FIG. 4a. In one embodiment, the healthcare practitioner implements the personalized treatment plan for the patient, said implementation includes, but is not limited to, prescription of lifestyle modification, prescription of one or more drugs, or a combination thereof. In one embodiment of the present invention, a lab technician utilizes the CVD risk protocol algorithm to perform diagnosis analysis utilizing the results of the extended CVD testing, and delivers the results of the analysis to a healthcare practitioner who interprets the diagnosis analysis results, and devises a treatment plan personalized to the patient based on the said interpretation of diagnosis analysis. In one embodiment, a healthcare practitioner utilizes the CVD risk protocol algorithm to perform diagnosis and treatment analysis utilizing the results of the extended CVD testing, as illustrated in FIG. 4b. In one embodiment, the healthcare practitioner implements the treatment plan resulting from the performance of the CVD risk protocol algorithm. In another embodiment, the healthcare practitioner modifies the treatment plan obtained from the performance of the CVD risk protocol algorithm and implements the modified plan for the patient. In one embodiment of the present invention, a healthcare practitioner monitors the effectiveness of one or more aspects of the personalized treatment plan on a patient. The healthcare practitioner may modify the personalized treatment plan based on the patient's response thereto, which may be, but is not limited to, inadequate effectiveness on one or more aspects of the CVD or CVD risk, undesirable or intolerable side effect(s), or a combination thereof. The monitoring may be conducted over a short term e.g., weeks, or long term, e.g., months or years, of time; the monitoring may be conducted in recurring periods of time in a given short term or long term time period. The patient may be re-tested with the present extended testing panel during the course of monitoring the effectiveness of the personalized treatment plan, said course of monitoring may extend to the remainder of the patient's life.

The present invention provides certain unique features not available with currently existing tests for CVD risk assessment, said features include a comprehensive CVD risk assessment and individualized treatment planning. Further, the use of the extended risk panel and the CVD risk protocol algorithm disclosed herein to diagnose a patient based on comprehensive data obtained from the extended testing provides synergistic advantages over the use of limited test panels, in terms of efficiency, greater accuracy of diagnosis, cost savings, and the shortened period of time to diagnose and treat a patient according to a personalized plan. These advantages of the present invention also remain when compared to diagnosis made singly (versus comprehensively, as with the methods of the present invention) based on results obtained from the use of a limited test panel, even if several different limited test panels are used (thus, resulting in multiple singly made diagnosis, and potentially conflicting or inaccurate diagnosis), particularly when such testing is conducted at varying periods of time, and even if the several limited test panels used would cover all of the tests included in the extended risk panel of the present invention. The inclusion of HDL subpopulation analysis by two-dimensional gel electrophoresis, CRP molecular forms, sdLDL-C, and plasma sterol testing in the extended risk panel particularly contributes to said uniqueness. The various aspects of the present invention are described hereinbelow in sections 3.1-3.3; the information pertaining to test results that is disclosed in these sections is utilized in combination to make a comprehensive diagnosis and create an individualized treatment plan for a patient. Further, information in sections 3.1-3.3 contain statistical data that forms the basis for comparison of a patient's test results thereto, said data being provided as a part of the algorithm to facilitate the performance of diagnosis analysis or diagnosis and treatment analysis.

3.1 Use of HDL Information

The methods of diagnosis and treatment of the present invention utilize the findings of the Adult Treatment Panel III (ATP III) of the National Cholesterol Education Program (NCEP-ATP III) [as published in 2001: "Executive Summary of The Third Report of The National Cholesterol Education Program (NCEP) Expert Panel on Detection, Evaluation, And Treatment of High Blood Cholesterol In Adults (Adult Treatment Panel III). Expert Panel on Detection, Evaluation, and Treatment of High Blood Cholesterol in Adults", *JAMA*, 2001, May 16; 285(19):2486-97; with an update published in 2004: "Implications of Recent Clinical Trials for the National Cholesterol Education Program Adult Treatment Panel III Guidelines", Grundy, S. M., et. al.; National Heart, Lung, and Blood Institute; American College of Cardiology Foundation; American Heart Association. *Circulation,* 2004, Jul. 13; 110(2):227-39]. Accordingly, the primary goal of lipid modifying therapy is to achieve specified LDL cholesterol targets. Means of achieving this goal include therapeutic life style changes (TLC) and drug therapy with a statin. If additional lipid parameters need modification, then agents such as ezetimibe, niacin, resins, fibrates, and fish oil preparations are used. The secondary goal of lipid modifying therapy is to achieve specified TG and HDL targets. Means to achieve this goal include the use of therapeutic agents, preferably, one or more fibrates, nicotinic acid, and fish oil.

It has been established that a level of HDL-C that is less than 40 mg/dL in men and less than 50 mg/dL in women is considered low; an HDL-C rise of 1 mg/dL has been associated with a 1-2% reduction in CVD events; and an optimal level of HDL cholesterol is greater than 60 mg/dl in both men and women. However, HDL particle analysis provides greater precision in CHD risk prediction. A 26% reduction in CVD events is observed when the large α-1 HDL apoA-I particle is increased by 1 mg/dl. The present invention involves "HDL fingerprinting"—the analyses of HDL apoA-I sub particles with the two-dimensional gel electrophoresis method, as described above, and the evaluation of the data acquired therefrom to optimize treatment as outlined below.

1. The present invention utilizes the information from HDL fingerprinting in the following manner:
    a. In patients with low HDL-C (<40 in men, <50 in women): Low HDL-C is a significant CVD risk factor. Knowledge about HDL fractions provides information on HDL particle distribution and enables more precise CHD risk assessment than HDL-C measurement alone. Moreover, HDL fingerprinting provides indicators to enable a more precise determination of which specific treatment option may be most effective in optimizing HDL particle distribution. Without the information gathered from HDL fingerprinting, the recommended therapy for all patients, regardless of any unique circumstances of any given patient, would be to increase the HDL-C level. The HDL fingerprinting information adds another dimension to a patient's therapy that greatly increases their likelihood of receiving successful therapy; as such therapy would be individualized for that patient.
    b. In patients with optimal HDL-C: Patients with optimal HDL-C level may have increased level of the small, lipid-poor preβ-1 HDL particle and decreased level of the large lipid-rich HDL sub particle. Both of these patterns indicate an inadequate HDL metabolism and increased risk for cardiovascular disease. The ratio of the most athero-protective (α-1) to the less athero-protective (α-3, α-4, and preβ-1) HDL sub particles indicates whether HDL function is normal or abnormal.

2. The present invention utilizes the following information regarding five of the apoA-I-containing HDL sub fractions (α-1, α-2, α-3, α-4 and preβ-1) in the determination of treatment:
    a. α-1: a low α-1 level is the best indicator for cardiovascular risk in patients who have no previous history of cardiovascular events.
    b. α-2: a low α-2 level is the best indicator of cardiovascular risk in patients with a past history of cardiovascular events.
    c. α-3: a low α-1 to α-3 ratio (<0.3) indicates insufficient HDL metabolism and reflects a triglyceride metabolism problem.
    d. α-4: a low α-1 to α-4 (<0.6) ratio indicates insufficient HDL metabolism and reflects a cholesterol esterification problem.
    e. preβ-1: a high preβ-1 level (greater than (">") 20 mg/dl) is associated with increased risk for cardiovascular disease. The ratio of α-1 to preβ-1 is the best indicator of HDL function; a decreased ratio (<0.5) reflects an increased cholesteryl ester transfer protein (CETP) activity or imbalance between lecithin:cholesterol acyltransferase (LCAT) and CETP activity.

3. The following represent, but not limited to, various diagnostic and treatment embodiments of the present invention:
    a. Test Results: An HDL fingerprint, marked with high levels of α-1 HDL and α-2 HDL together with low levels of preβ-1 HDL, α-3 HDL, and α-4 HDL.
       Diagnosis: Decreased CVD risk in the vast majority of cases.
       Treatment: None necessary.
    b. Test Results: No apoA-I present in plasma.
       Diagnosis: ApoA-I deficiency.
       Treatment: Limited to infusion of HDL mimetic, such as preβ-1 HDL, or similar apoA-I compounds that may promote cellular free cholesterol efflux to reduce risk for CVD.
       Additional treatment: Optimize other risk factors, such as smoking, high blood pressure, diabetes, LDL-C, TG, and CRP.
    c. Test Results: ApoA-I is present only in preβ-1 HDL.
       Diagnosis: ABCA1 deficiency (Tangier disease).
       Treatment: Optimize other risk factors (as stated hereinabove).
    d. Test Results: Very low levels of apoA-I (<20 mg/dl) and HDL-C (<10 mg/dl), and apoA-I present in preβ-1 HDL and α-4 HDL.
       Diagnosis: Lecithin cholesterol acyltransferase (LCAT) deficiency.
       Treatment: Optimize other risk factors (as stated hereinabove) and monitor for renal insufficiency and anemia.
    e. Test Results: Low levels of HDL-C (<25 mg/dl) and apoA-I (<70 mg/dl) and very low levels of the large α-1 (<5%) and α-2 (<25%) HDL particles, but normal levels of preβ-1, α-4, and α-3 HDL particles.
       Diagnosis: Can be heterozygous apoA-I deficiency, ABCA1 deficiency, or LCAT deficiency (different familial forms of low HDL).

Treatment: Optimize all other risk factors (as stated hereinabove), and increase HDL apoA-I level with the use of niacin.
f. Test Results: There is only preβ-1 HDL and low levels of amorphous α-HDL; TG level greater than 1000 mg/dL.
  Diagnosis: Lipoprotein lipase (LPL) deficiency.
  Treatment: Restrict fat intake (<15% of calories from fat), but recommend a diet enriched in essential fatty acids.
g. Test Results: Low level of HDL-C (<40 mg/dl in men, <50 mg/dl in women), low level of α-1 HDL (<13 mg/dl in men, <20 mg/dl in women), high level of TG (>150 mg/dl) and high level of preβ-1 HDL (>15 mg/dl).
  Diagnosis: This pattern is frequently seen and indicates increased CETP activity. Increased CETP activity can be the result of high triglyceride-rich lipoproteins that is the primary substrate for CETP.
  Treatment: As follows:
  I. The first choice is to recommend lifestyle changes (weight loss if obese, diet and exercise) as well as optimizing other risk factors (as stated hereinabove). HDL profile typically can be improved more with significant weight loss than with any statin monotherapy.
  II. The second choice is therapy with a statin, to decrease LDL-C and TG levels, increase HDL-C level, and shift the HDL subpopulation profile beneficially (decreasing pre-β1 and increasing α-1). Statin effectiveness, in order to change the HDL particle profile beneficially, from least effective to most effective, is: fluvastatin (adverse effect), lovastatin (almost no change), pravastatin, simvastatin, atorvastatin and rosuvastatin. Rosuvastatin, atorvastatin, and simvastatin are the most effective statins in decreasing order for increasing the large α-1 HDL level and decreasing the small dense LDL level. However, there is a considerable variation in individual response. Moreover, despite the higher LDL-C decreasing capacity of 80 mg/day atorvastatin versus the 40 mg/day atorvastatin, the higher dose has less capacity for increasing the α-1 HDL level than the lower dose.
  III. If the LDL cholesterol goal (i.e., <70 mg/dl in heart disease patients) is not achieved, then, increase the statin dose, or use a more effective statin, or add ezetimibe.
  IV. If LDL goal is reached but HDL-C and α-1 HDL levels are low, then, statin-niacin combination therapy is recommended. Niacin increases apoA-I production and the levels of HDL-C, apoA-I, and α-1 HDL particles, while decreasing the levels of TG and preβ-1 HDL particles.
  V. If LDL goal is not reached with a potent statin, a statin-ezetimibe combination therapy is recommended. Statin decreases cholesterol synthesis in the liver and ezetimibe decreases cholesterol absorption in the intestine.
  VI. In case of high level of cholesterol synthesis markers (lathosterol and desmosterol), statin therapy is the best choice.
  VII. In case of a high level of cholesterol absorption markers (elevated campesterol and β-sitosterol), the statin-ezetimibe combination treatment is the best option.
h. Test Results: Low α-1 HDL level, and normal TG and LDL-C levels.
  Diagnosis: Likely a genetic disorder.
  Treatment: Niacin therapy to increase apoA-I production.
i. Test Results: Normal to high HDL-C level, very high α-1 HDL level, and symptoms of CVD.
  Diagnosis: Possible problem with scavenger receptor B1 (SRB1) mediated uptake of HDL by the liver due to decreased scavenger receptor B1 function. HDL-mediated reverse (direct) cholesterol transport or HDL remodeling is slowed by decreased SRB1 function.
  Treatment: There is no specific medication available yet for increasing SRB1 function; however, this invention contemplates the use of a specific medication for increasing SRB1 function if and when such a medication becomes available. Due to a lack of a specific medication, current recommendation is aggressive lipid lowering strategy. No medication is necessary to further increase HDL-C or α-1 HDL levels.
j. Test Results: Normal to moderately increased TG level, normal LDL-C level, and slightly decreased HDL-C level, but low α-1 HDL and high preβ-1 HDL levels.
  Diagnosis: Isolated hypertriglyceridemia.
  Treatment: Fish oil, and/or niacin therapy. Medication with a fibrate, such as gemfibrozil, can be an alternative treatment.
k. Test Results: Level of hsCRP greater than 3 mg/L and less than 10 mg/L.
  Diagnosis: Increased heart disease risk.
  Treatment: Statin or a salicylate therapy to reduce hsCRP levels to less than 2 mg/L.
l. Test Results: Level of hsCRP greater than 10 mg/L and low α-1 HDL level.
  Diagnosis: The patient may have an acute infection, and testing should be performed again at a later date.
4. Specific effects of pharmacological agents are as follows:
  a. Statins decrease cholesterol synthesis, lower Tg-rich lipoprotein (TRL) apoB and LDL apoB levels by increasing their FCR (fractional catabolic rate), have little effect on HDL apoA-I and apoA-II metabolism, but increase large HDL particle level by lowering TRL, and decreasing cholesteryl ester transfer from HDL to TRL. The best statins to increase α-1 HDL and decrease preβ-1 HDL levels (in the order of most beneficial to least beneficial) are rosuvastatin>atorvastatin>simvastatin>pravastatin>lovastatin>fluvastatin. Rosuvastatin and atorvastatin also significantly decrease preβ-1 HDL level by decreasing CETP activity, but have little or no effect on apoA-I kinetics.
  b. Ezetimibe inhibits intestinal cholesterol absorption, and is particularly effective in patients who are hyperabsorbers whether they are off therapy or on statin therapy. Ezetimibe is very useful for lowering LDL-C when added to statin therapy. This drug is also effective in patients with phytosterolemia who have inherited defects resulting in excess absorption of plant sterols.
  c. Resins, such as colestipol, are useful for lowering LDL-C levels when added to statin therapy.
  d. Fibrates increase levels of HDL-C (by 4-6%) and α-3 HDL (by 4-6%), mainly increase the level of apoA-II, increase gene expression of apoA-I, apoA-II, LPL; but fibrates also enhance apoA-I fractional catabolic rate (FCR), and therefore have little effect on apoA-I concentration. Fibrates are very useful in lowering the elevated level of triglycerides, as well as decreasing CVD risk in those with elevated insulin levels.

e. Niacin increases HDL and large HDL particles by increasing apoA-I production, lowers TRL and apoB levels by causing an increased FCR, and also markedly raises adiponectin level. The use of the combination of niacin and simvastatin was found to increases α-1 HDL by 115% (in the HDL Atherosclerosis Treatment Study population—increases in this fraction were significantly and inversely associated with less progression in coronary artery stenosis ["Change in α-1 HDL concentration predicts progression in coronary artery stenosis", Asztalos, B. F., et. al., *Arterioscler Thromb Vasc Biol.*, 2003, 847-852]). Niacin therapy is ideal in combination with statin therapy in CHD patients who have low HDL-C and α-1 HDL particle levels.

f. Omega 3 fatty acids, as found in fish oil preparations, are useful in lowering triglycerides, and also in improving HDL particle profiles to reduce CVD risk.

3.2 Use of Plasma Sterol Information

The methods of diagnosis and treatment of the present invention utilize the information gathered from testing of plasma sterols. In one embodiment of the present invention, plasma sterol information is used for diagnosis and treatment in the following manner:

Test Results: Elevated cholesterol synthesis marker.

Diagnosis: Over production of cholesterol in patients who have high levels of lathosterol (please refer to Table 1 and Table 2 below).

Treatment: High dose of an effective statin is ideal.

In one embodiment of the present invention, plasma sterol information is used for diagnosis and treatment in the following manner:

Test Results: Elevated cholesterol absorption markers in patients who have high or very high levels of B-sitosterol and campesterol (please refer to Table 1 and Table 2 below).

Diagnosis: High dietary-cholesterol absorption in the gut, which is usually accompanied with low cholesterol synthesis.

Treatment: If the LDL cholesterol is not at goal, then add ezetimibe to decrease cholesterol absorption. Ezetimibe is best used in combination with a statin but can also be used as monotherapy or in combination with any other lipid modifying agent, such as a niacin or a fibrate.

In one embodiment of the present invention, plasma sterol information is used for diagnosis and treatment in the following manner:

Test Results: Elevated lathosterol (>150 moles×$10^2$ mol of cholesterol) and desmosterol values (>80 moles×$10^2$ mol of cholesterol), which indicate increased cholesterol levels. Elevated beta-sitosterol (>160 moles×$10^2$ mol of cholesterol) and campesterol (>300 moles×$10^2$ mol of cholesterol) values, which indicate increased absorption of cholesterol.

Diagnosis 1: Phytosterolemia, due to over absorption of the plant sterols beta sitosterol and campesterol. It is diagnosed by the finding of beta-sitosterol value greater than 250 moles×$10^2$ mol of cholesterol and campesterol value greater than 400 moles×$10^2$ mol of cholesterol. Patients with this diagnosis develop premature heart disease.

Treatment 1: Primary treatment is aggressive statin therapy. If the patient is not at his or her LDL cholesterol goal while on statin therapy, then ezetimibe, an inhibitor of both cholesterol and plant sterol absorption, should be added to the regimen. Therapy with an ezetimibe can also be used as a primary treatment.

Diagnosis 2: Cerebrotendinous Xanthomatosism, which is due to abnormal bile acid metabolism, is diagnosed by the finding of cholestanol level greater than 250 moles×$10^2$ mol of cholesterol. Patients with this diagnosis have tendinous xanthomas, and develop neurologic diseases if their cholestanol level is not well controlled.

Treatment 2: Therapy with 250 mg of chenodeoxycholate, orally administered three times a day (total daily dose of 750 mg).

TABLE 1

Sterol Reference Values in Women

| Women | Synthesis markers | | Absorption markers | | |
|---|---|---|---|---|---|
| | Lathosterol | Desmosterol | B-sitosterol | Campesterol | Cholestanol |
| Optimal | <130 | <70 | <130 | <180 | <130 |
| Borderline | 130-150 | 70-80 | 130-160 | 180-300 | 130-160 |
| High | >150 | >80 | >160 | >300 | >160 |
| Very high | >200 | >150 | >250 | >400 | >250 |

(Sterol values in moles × $10^2$ mol of cholesterol)
(The symbol < signifies 'less than', and the symbol > signifies 'greater than')

TABLE 2

Sterol Reference Values in Men

| Men | Synthesis markers | | Absorption markers | | |
|---|---|---|---|---|---|
| | Lathosterol | Desmosterol | B-sitosterol | Campesterol | Cholestanol |
| Optimal | <120 | <70 | <150 | <200 | <130 |
| Borderline | 120-135 | 70-75 | 150-160 | 200-220 | 130-140 |
| High | >135 | >75 | >160 | >300 | >160 |
| Very high | >200 | >150 | >250 | >400 | >250 |

(Sterol values in moles × $10^2$ mol of cholesterol)
(The symbol < signifies 'less than', and the symbol > signifies 'greater than')

3.3 Use of CRP Molecular Form Information

Figure 2:
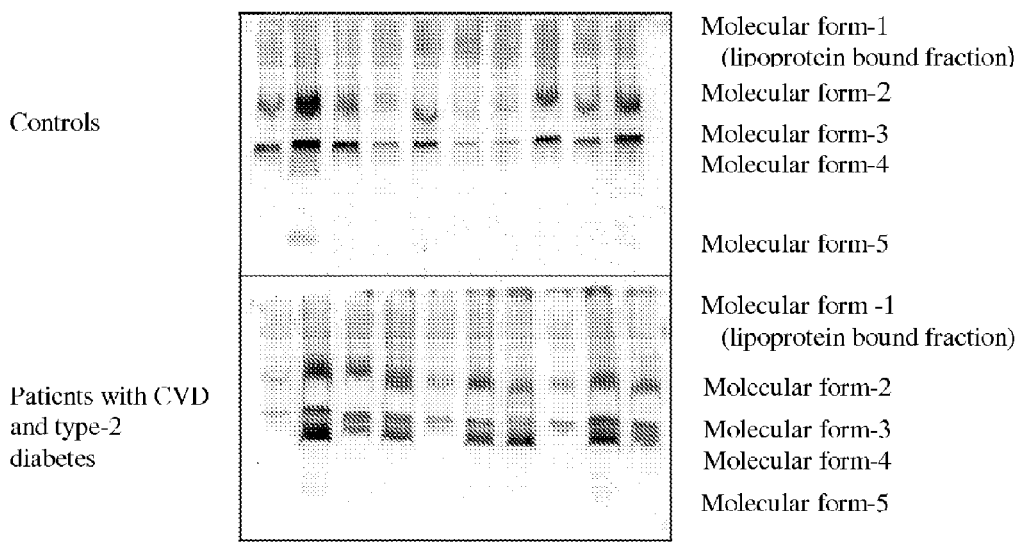
FIG. 2 illustrates non-denaturating one-dimensional gel electrophoresis of whole plasma, followed by immunoblotting with specific antibody for CRP, according to an embodiment of the present invention. The gels shown document the presence of five individual molecular forms of CRP. The CRP patterns of controls are shown in the top panel, while the patterns observed in obese, diabetic patients with CVD are shown in the lower panel. The major difference between CVD cases and controls is the presence of CRP molecular form 4 in the CVD cases.

The methods of diagnosis and treatment of the present invention utilize the information gathered from gel electrophoresis testing. Table 3 (below) illustrates the distribution of CRPmf in male subjects. Those patients with clinical signs of CVD or diabetes (DM) have higher levels of CRPmf-4 than patients without clinical signs of CVD or diabetes. However, subjects with metabolic syndrome have the highest level of CRPmf-4. The presence of the CRP molecular form-4 being associated with an increased CVD risk in subjects who are obese and/or diabetic, is further illustrated in FIG. 2 (showing CRP molecular forms for representative male populations, those who are normal (indicated as "control", no clinical signs of CVD) and those who are obese and diabetic with clinical signs of CVD.

In one embodiment of the present invention, where CRPmf-4 is present in an obese patient, aggressive weight loss is recommended. In another embodiment, where CRPmf-4 is present in a diabetic patient, statin therapy is recommended for reducing LDL cholesterol and TG levels. In another embodiment, where CRPmf-4 is present in a diabetic and obese patient, weight loss and statin therapy is recommended.

TABLE 3

Percent Distribution of The Most Common CRP Molecular Forms in Different Male Populations

| N = 40 in each group | CRPmf-1 | CRPmf-2 | CRPmf-3 | CRPmf-4 |
|---|---|---|---|---|
| Male control | 31 ± 15 | 35 ± 7 | 28 ± 7 | 7 ± 11 [30] |
| Male CVD | 26 ± 14 | 40 ± 6 | 20 ± 6 | 15 ± 14 [57] |
| Male CVD + DM | 21 ± 13 | 32 ± 7 | 26 ± 9 | 22 ± 16 [77] |
| Metabolic syndrome, no CVD | 22 ± 14 | 30 ± 7 | 25 ± 7 | 21 ± 13 [100] |

(Values were calculated as percent distribution and presented as mean ± SD)
(Numbers in [ ] represent the percentile of those subjects who have >5% of CRPmf-4)

As noted above, the present invention pertains to an extended cardiovascular disease risk assessment panel for testing and measuring the combination of traditional risk factors and new important risk factors, and to methods for personalized diagnosis and treatment utilizing a CVD diagnosis and treatment protocol algorithm and the results of the extended risk assessment testing. The present invention should not be considered limited to the particular embodiments described above, but rather should be understood to cover all aspects of the invention as fairly set out in the appended claims. Various modifications, equivalent processes, as well as numerous structures to which the present invention may be applicable will be readily apparent to those skilled in the art to which the present invention is directed upon review of the present application. The claims are intended to cover such modifications.

We claim:

1. A method for determining a cardiovascular disease (CVD) diagnosis and a personalized treatment for a patient, the method comprising
obtaining one or more samples from a patient;
measuring the one or more samples for levels of a plurality of HDL subfractions selected from the group consisting of α-1, α-2, α-3, α-4, and preβ-1 to create an HDL fingerprint, and when the HDL fingerprint indicates that the patient should be treated, then measuring the one or more samples for levels of:
at least one marker of cholesterol absorption and at least one marker of cholesterol production, wherein the marker of cholesterol absorption is selected from the group consisting of beta-sitosterol and campesterol, and the marker of cholesterol production is lathosterol;
comparing the levels of the marker of cholesterol absorption and the marker of cholesterol production to corresponding reference levels;
classifying based on the comparison if the patient is a hypo-absorber, a hyper-absorber, an over-producer, a normal-producer of cholesterol or a combination thereof, wherein a level of lathosterol greater than the reference level indicates that the patient is an over-producer and a level of beta-sitosterol or campesterol higher than a corresponding reference level indicates that the patient is a hyper-absorber;
determining a CVD diagnosis and a personalized therapy in response to the patient's classification when the patient's HDL fingerprint indicates that the patient should be treated.

2. The method of claim 1, wherein the personalized therapy comprises administering an ezetimibe.

3. The method of claim 1, wherein the sample is a blood sample.

4. The method of claim 1, wherein a level of lathosterol greater than a reference level indicates that the patient should be administered a statin therapy.

5. The method of claim 1, wherein a high level of beta-sitosterol indicates that the patient is a hyper-absorber, wherein the high level of beta-sitosterol is greater than 160 mmol×$10^2$/mol of cholesterol.

6. The method of claim 1, wherein a high level of campesterol indicates that the patient is a hyper-absorber, wherein the high level of campesterol is greater than 300 mmol×$10^2$/mol of cholesterol.

* * * * *